US006951649B2

(12) United States Patent
Smith et al.

(10) Patent No.: US 6,951,649 B2
(45) Date of Patent: *Oct. 4, 2005

(54) METHODS OF MAKING NEURAMINIDASE-SUPPLEMENTED COMPOSITIONS

(75) Inventors: Gail Eugene Smith, Wallingford, CT (US); James T. Matthews, Allamuchy, NJ (US); Edwin D Kilbourne, Madison, CT (US); Bert E. Johansson, Armonk, NY (US); Bethanie E. Wilkinson, Higganum, CT (US); Andrie I. Voznesensky, West Hartford, CT (US); Craig S. Hackett, Wallingford, CT (US); Franklin Volvovitz, Woodridge, CT (US)

(73) Assignee: Protein Sciences Corporation, Meridien, CT (US)

( * ) Notice: Subject to any disclaimer, the term of this patent is extended or adjusted under 35 U.S.C. 154(b) by 75 days.

This patent is subject to a terminal disclaimer.

(21) Appl. No.: 10/264,813

(22) Filed: Oct. 4, 2002

(65) Prior Publication Data

US 2003/0165521 A1 Sep. 4, 2003

Related U.S. Application Data

(60) Division of application No. 09/372,734, filed on Aug. 11, 1999, now Pat. No. 6,485,729, and a continuation-in-part of application No. 09/235,901, filed on Jan. 22, 1999, now abandoned, and a continuation-in-part of application No. 09/169,027, filed on Oct. 9, 1998, now Pat. No. 6,245,532, and a continuation-in-part of application No. 08/843,519, filed on Apr. 16, 1997, now abandoned, which is a division of application No. 08/453,848, filed on May 30, 1995, now Pat. No. 5,858,368, which is a continuation-in-part of application No. 08/430,971, filed on Apr. 28, 1995, now Pat. No. 5,976,552, which is a continuation-in-part of application No. 08/120,607, filed on Sep. 13, 1993, now Pat. No. 5,762,939.

(51) Int. Cl.⁷ ..................... A61K 39/145; A61K 39/295
(52) U.S. Cl. ............................... 424/210.1; 424/206.1; 424/201.1
(58) Field of Search ........................ 424/210.1, 206.1, 424/201.1; 436/17

(56) References Cited

U.S. PATENT DOCUMENTS

| 4,247,539 | A | * | 1/1981 | Iritani et al. | ................. | 530/350 |
|---|---|---|---|---|---|---|
| 4,631,191 | A | | 12/1986 | Dale et al. | | |
| 4,693,893 | A | | 9/1987 | Campbell | | |
| 5,728,385 | A | | 3/1998 | Classen | | |
| 5,962,298 | A | | 10/1999 | Fiers | | |
| 5,976,552 | A | | 11/1999 | Volvovitz | | |
| 6,485,729 | B1 | * | 11/2002 | Smith et al. | ............. | 424/210.1 |

OTHER PUBLICATIONS

Webster et al. Potentation of the Immune Response to Influenza Virus Subunit Vaccines J. Immunology (1997) vol. 199 (6) pp. 2073–2077.

Kuroda et al. Expression of the Influenza Virus Haemagglutinin in Insect Cells by a Baculovirus Vector EMBO Journal vol. No. 6 pp. 1359–1365, 1986.

Connaught Laboratories Inc. Rabies Immune Globulin 90B Physicians Desk Reference, 1995 (Medical Economics Data Production Company, Montvale, NJ).

Mather et al. Expression of Influenza Neuraminidase in Baculovirus–Infected Cells, Virus Research, 26(2): 127–139, 1992.

Hausmann, et al. "N1 neuraminidase of influenza virus A/FPV/Rostock/34 has haemadsorbing activity," Journal of General Virology 76: 1719–1728, 1995 abstract only.

Johansson, et al. "Immunogenicity of influenza A virus N2 neuraminidase produced in insect larvae by baculovirus recombinants," Vaccine, vol. 13, No. 9. pp. 841–845, 1995.

Deroo, et al. "Recombinant neuraminidase vaccine protects against lethal influenza," Vaccine, vol. 14, No. 6, pp. 561–569, 1996.

Yue–xin, et al. "Expression of Neurominidase of Influenza Virus in Insect Cells," Chinese Journal of Biochemistry and Biophysics, vol. 25, No.4, pp. 237–241, 1992 (reprinted 1993 in Englsh).

* cited by examiner

Primary Examiner—Marjorie Moran
(74) Attorney, Agent, or Firm—Frommer Lawrence & Haug LLP; Thomas J. Kowalski; Angela M. Collison

(57) ABSTRACT

The present invention relates to a method for formulating a vaccine composition which comprises an anti-influenza vaccine, wherein the improvement of the vaccine composition is that the vaccine includes, as an additive, neuraminidase (NA). The base anti-influenza vaccine can be any commercially available anti-influenza vaccine. The improved composition can include and be administered with an adjuvant. The improved vaccine composition provides protection in a host, animal or human, against influenza infection, including viral replication and systemic infection.

10 Claims, 3 Drawing Sheets

METHODS OF MAKING NEURAMINIDASE-SUPPLEMENTED COMPOSITIONS

RELATED APPLICATIONS

Figure 1:
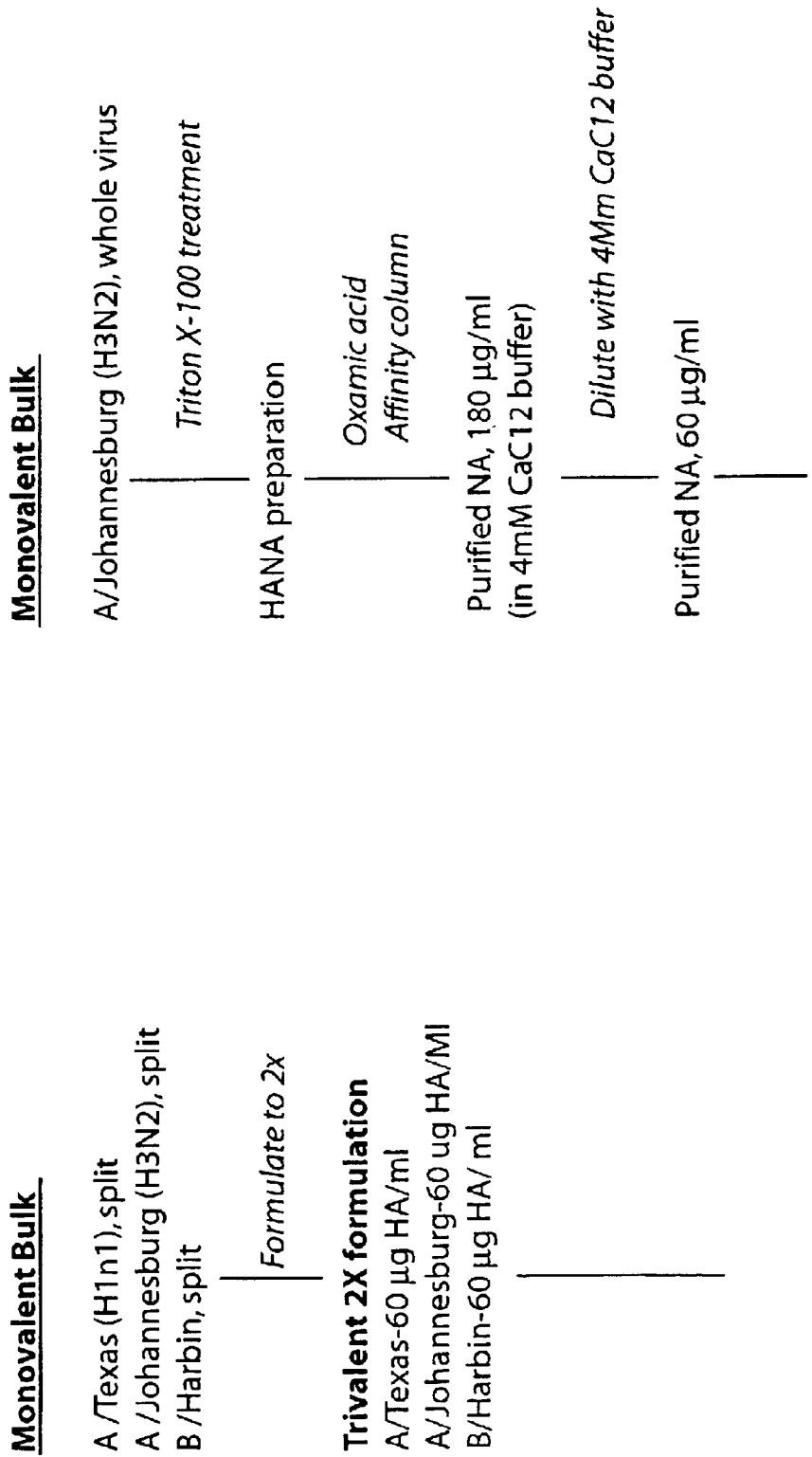
Figure 2:
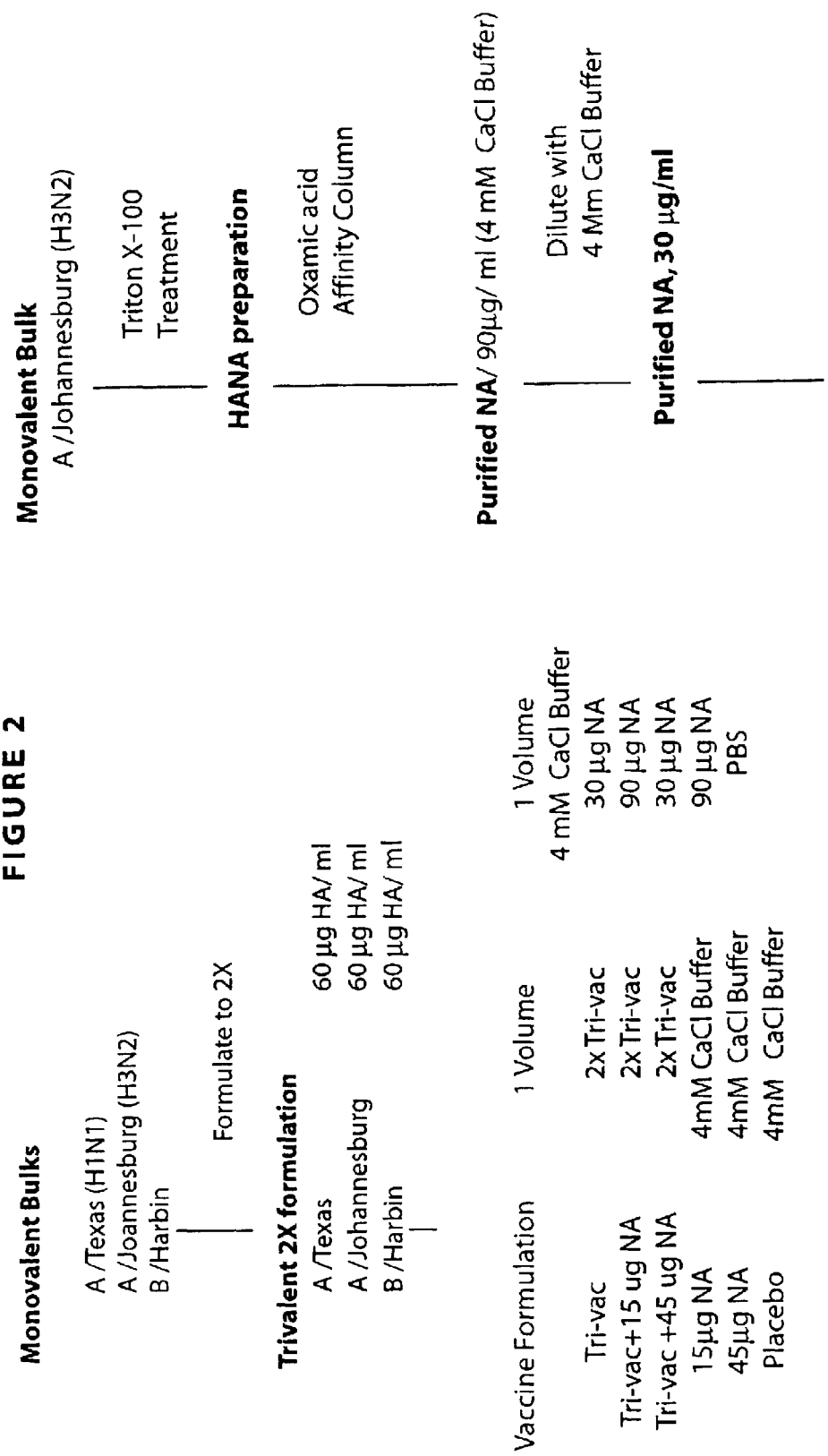
Figure 3:
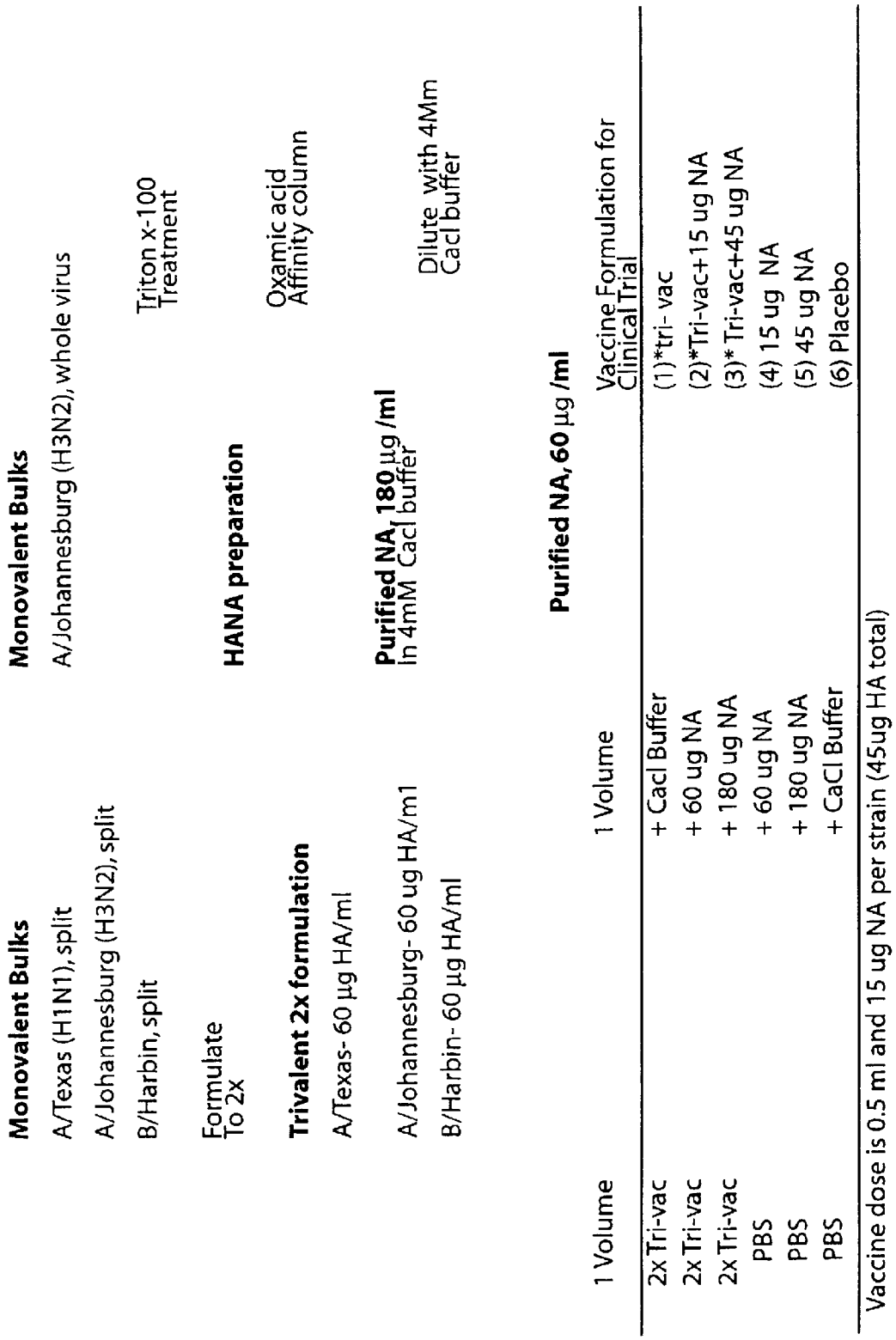

This application is a divisional of U.S. application Ser. No. 09/372,734, filed Aug. 11, 1999 now U.S. Pat. No. 6,485,729, which is a continuation-in-part of: U.S. application Ser. No. 08/430,971, filed Apr. 28, 1995 (now U.S. Pat. No. 5,976,552); and is a C.I.P. of U.S. application Ser. No. 09/235,901, filed Jan. 22, 1999 now abandoned; U.S. application Ser. No. 09/169,027, filed Oct. 9, 1998 (now U.S. Pat. No. 6,245,532), which is a divisional of U.S. application Ser. No. 08/453,848, filed May 30, 1995 (now U.S. Pat. No. 5,858,368), which is a continuation-in-part of U.S. application Ser. No. 08/120,607, filed Sep. 13, 1993 (now U.S. Pat. No. 5,762,939); and, U.S. application Ser. No. 08/843,519, filed Apr. 16, 1997 (now abandoned). The disclosures of all these applications and Patents, the references cited therein and the references cited during the prosecution of those applications and Patents, as well as the references cited herein, are all expressly incorporated herein by reference.

FIELD OF THE INVENTION

The present invention relates to a Neuraminidase (NA) supplemented compositions, and methods employing the same, including routes of administration. More specifically, the present invention relates to an immunological, antigenic, immunogenic, or vaccine composition comprising an anti-influenza vaccine wherein the improvement comprises having as an additive neuraminidase (NA) from at least one influenza virus strain; and, to methods for making and using the same. Such compositions and methods have advantages such as improved efficacy.

Several documents are cited in the text, with full citation thereat, or in the portion headed "References", and each document cited herein ("herein cited documents") and each document referenced or cited in herein cited documents are hereby incorporated herein by reference.

BACKGROUND OF THE INVENTION

The influenza viruses are divided into types A, B and C based on antigenic differences. Influenza A viruses are described by a nomenclature which includes the sub-type or type, geographic origin, strain number, and year of isolation, for example, A/Beijing/353/89. There are at least 15 sub-types of HA (H1–H13) and nine subtypes of NA (N1–N9). All subtypes are found in birds, but only H1–H3 and N1–N2 are found in humans, swine and horses (Murphy and Webster, "Orthomyxoviruses", in *Virology*, ed. Fields, B. N., Knipe, D. M., Chanock, R. M., 1091–1152 (Raven Press, New York, 1990)). Influenza A and B virus epidemics can cause a significant mortality rate in older people and in patients with chronic illnesses.

Epidemic influenza occurs annually and is a cause of significant morbidity and mortality worldwide. Children have the highest attack rate, and are largely responsible for transmission of influenza virus in the human community. The elderly and persons with underlying health problems, e.g., immuno-compromised individuals, are at increased risk for complications and hospitalization from influenza infection. In the United States alone, more than 10,000 deaths occurred during each of the seven influenza seasons between 1956 and 1988 due to pneumonia and influenza, and greater than 40,000 deaths were reported for each of the two seasons (Update: Influenza Activity—United States and Worldwide, and Composition of the 1992–1993 Influenza Vaccine, *Morbidity and Mortality Weekly Report*. U.S. Department of Health and Human Services, Public Health Service, 41/No. 18:315–323, 1992).

The influenza vaccines currently used are inactivated vaccines: they may be constituted of entire virions, or of virions subjected to treatment with agents which dissolve lipids ("split" vaccines), or else of purified glycoproteins ("sub-unit vaccines"). These inactivated vaccines mainly protect by causing synthesis of the receiver's antibodies directed against the hemagglutinin. Antigenic evolution of the influenza virus by mutation results in modifications in HA and NA. Accordingly, inactivated vaccines used at present only protect against strains having surface glycoproteins which comprise identical or cross-reactive epitopes. To provide a sufficient antigenic spectrum, conventional vaccines comprise components from several viral strains; they generally contain two type A strains and one type B strain. The choice of strains for use in vaccines is reviewed annually for each particular year and is predicated on WHO FDA recommendations. These recommendations reflect international epidemiological observations. Viral strains may be obtained from:

NIBSC (National Institute for Biological Standards and Control, London, UK).

WIC (World Influenza Centre, London, UK).

CDC (Centers for Disease Control, Atlanta, USA).

CBER (Center for Biologics Evaluation and Research, Washington, USA).

Current influenza virus seeds for vaccine production must be shown to have the appropriate HA antigen because of the reassortant procedure used to generate high yielding virus strains used for manufacturing. However, there is currently no requirement for or limit to NA content in influenza vaccines. There is evidence that the NA level in vaccines is quite variable. Kendal et at. (Kendal et at., 1980) reported that the NA specific activity for different lots may range approximately 40-fold. Kendal et al. also noted a rapid decline of NA activity during six months of storage. As a result, the frequency of antibody response to NA was poor (mean seroconversion rate of 18%) compared to the HA response (seroconversion rate of 64%). The frequency of response to NA in a population known to be primed to that NA ranged from 0 to 32% compared to a response rate of 29 to 91% for the HA antigen (Palese, et al., 1982).

Commercially available conventional influenza vaccines include a trivalent subvirion vaccine which contains 15 μg/dose of each the Has from influenza A/Texas/36/91 (NINI), A/Beijing/32/92 (H3N2) and B/Panama, 45/90 viruses (FLUZONE™ attenuated flu vaccine, Connaught Laboratories, Swiftwater, Pa.). A purified virus surface antigen vaccine is sold as Fluvirin® (an attenuated influenza viral vaccine produced by culturing in eggs). Each conventional vaccine can contain 15 micrograms of viral HA per 0.5 ml from A/Texas/36/91 (HINI), A/Shangdong/9/93

(H3N2), and B/Panama/45/90 influenza strains. Conventional vaccines generally contain 10 to 15 µg of hemagglutinin from each of the strains entering into their composition.

Previous clinical trials demonstrated that antibody to NA may be effective in inducing partial protection and in reducing the severity of illness. Examples are: Human Clinical Trials of NA specific vaccines. Clinical trials of NA-based vaccines consisted of NA-specific whole-viral antigenic hybrids containing the NA of interest and an irrelevant HA. In the first study, Couch et al. (Couch, R. B., et al., 1974) demonstrated reduction of viral replication and protection by an H7N2 virus vaccine in volunteers challenged with H3N2 virus and also showed solid resistance to reinfection and illness in subjects challenged six months later with the original virus.

In a two year study of 875 Buffalo school children, Ogra et al. (Ogra, P. L., et al., 1977) compared the effects of two vaccines under conditions of natural exposure and successive challenge by the Port Chalmers and Victoria variants of H3N2 virus. The two vaccines, X-41 and X-42, were manufactured under identical conditions. The X-41 vaccine contained HA and NA antigens of the Port Chalmers strain (comparable to conventional vaccine) and X-42 was an H7N2 antigenic hybrid possessing the irrelevant HA of an equine virus. The outcome of natural infection, first with Port Chalmers virus then with Victoria/75 virus in two successive winters is shown in the table below.

The infection rate in the first winter was shown to be the same in control and NA-specific vaccine groups. As expected, X-41 (conventional vaccine) caused a greater initial reduction of illness, although a lesser but significant reduction was seen with the NA-specific vaccine. In the second winter, the efficacy of NA vaccination was evident in that infection as well as the disease rate in the X-42 vaccines was reduced.

| Vaccine | Serologic Infection Rate | Ill | Protection Ratio[a] |
|---------|--------------------------|-----|---------------------|
| Comparison of NA-Specific (X-42) and Conventional (X-41) Vaccines in School Children | | | |
| Natural Infection I (A/Port Chalmers H3N2) in 1975 | | | |
| X-41 (H3N2) | 70/300 (23%) | 28 (9%) | 69 |
| X-42 (H7N2) | 119/300 (40%) | 56 (18%) | 37 |
| Placebo | 123/300 (45%) | 82 (29%) | — |
| Natural Infection II (A/Victoria/75 H3N2) in 1976 | | | |
| X-41 (H3N2) | 35/220 (16%) | 9 (4%) | 80 |
| X-42 (H7N2) | 45/201 (22%) | 12 (6%) | 73 |
| Placebo | 73/185 (40%) | 38 (20%) | — |

[a] $\frac{(\% \text{ ill in placebo group} - \% \text{ ill in vaccine group})}{\% \text{ ill placebo}} \times 100$ A trial in Czechoslovakia by Vonka et al. (Vonka, V., et al., 1977) used an inactivated whole-virus vaccine prepared from an H1N2 reassortant. A total of 1,200 subjects were vaccinated and a comparable group served as controls. An increase in HA antibody was noted in a majority of sampled subjects and against N2 in slightly more than half. Three months after immunization, an A/Victoria (H3N2) epidemic occurred. Although numerous influenza cases occurred in the two populations, morbidity was significantly lower in the vaccinated subjects.

While these studies show benefit of NA immunization, the NA was always presented in association with an HA antigen. In view of the phenomenon of antigenic competition and dominance of HA over NA, no real effect of NA was demonstrated. There are additional studies regarding NA reported in Kilbourne et al. (1995) in Vaccine.

It is therefore desirable to improve the existing anti-influenza vaccines.

Further, even if NA may itself be protective, heretofore there has been no demonstration, or recognition, of any effect NA could confer in conjunction with conventional, primarily HA-based vaccines, especially in view of the dominance and competition phenomena.

OBJECTS AND SUMMARY OF THE INVENTION

An object of the present invention is a vaccine composition against influenza, with synergic effects, containing influenza virus NA as an additive to the influenza vaccine.

The present invention provides a vaccine against influenza containing the constituents of a conventional influenza vaccine and/or a recombinant or recombinants expressing such constituents, e.g., a recombinant expressing HA or recombinant HA, and, in addition, NA as a supplement; e.g., NA from at least one influenza virus strain and/or NA from expression by a vector in vivo and/or in vitro. For example, a conventional influenza vaccine or a recombinant influenza vaccine (e.g., a recombinant expressing HA or HA from recombinant expression) which additionally contains NA: from at least one influenza strain, and/or from in vitro expression of NA by a vector (with isolation and/or purification of the NA), and/or from a vector which expresses NA in vivo (e.g., a conventional influenza vaccine including a vector which expresses NA in vivo). The vector can be a recombinant virus or a DNA plasmid or naked DNA.

It is an object of the present invention to provide an anti-influenza composition with improved antigenic cross-reactivity for protection against antigenically-distant strains.

It is another object of the present invention to provide an anti-influenza composition having flexibility in modifying antigenic content for specific populations.

Accordingly, the present invention provides a vaccine, antigenic, immunogenic or immunological composition which is an anti-influenza composition; and, which further includes, as an additive neuraminidase (NA) and/or a vector which expresses NA in vivo.

That is, the present invention provides an improvement to prior anti-influenza compositions by providing a such a composition comprising additional NA, as an additive.

The vaccine composition to which NA and/or the vector is added can comprise a complete virion, or a sub-unit, or a split vaccine; or a purified surface antigen or trivalent (from influenza or from recombinant expression) vaccine; or a vector which expresses a purified surface antigen or epitope of interest, e.g., HA or an epitope of interest thereof, in vivo.

The NA can be from at least one influenza strain; and, can be from isolating NA from the virion, or by recombinant expression.

The NA can be present, or expressed in vivo, in an amount sufficient to elicit an immunological response, e.g., a protective immune response; preferably such a response which is an improvement over a conventional vaccine or immunological composition (e.g., to provide improved efficacy).

The NA can be present, or expressed in vivo, preferably in a molar ratio relative to hemagglutinin (HA) of: from about 0.05 to about 2.0; for instance, from about 0.05 to about 0.15, or from about 0.15 to about 0.3, or from about 0.3 to about 0.65, or from about 0.65 to about 1.0, or from about 1.0 to 2.0. Thus, for instance, if HA is present in an amount of about 15 ug, NA may be present, or expressed in vivo, preferably in amounts of about 1, 2.5, 5, 10, 15 or 30 ug. The NA can be from A and/or B strains; and, can be from mammalian and/or avian influenza, e.g., human, avian, swine and/or equine influenza.

A vector or recombinant expressing NA can be present in an inventive composition in an amount of about at least $10^{3.5}$ pfu; more preferably about -continued Results of Hemagglutination-Inhibition Tests that Demonstrate Antigenic Drift of Influenza Type A(H3N2) Viruses from 1968 to 1986

| | Post-infection ferret sera to indicated reference virus | | | | | | | | |
|---|---|---|---|---|---|---|---|---|---|
| Reference Antigen | 1 | 2 | 3 | 4 | 5 | 6 | 7 | 8 | 9 |
| 3. A/Port Chalmers/1/73 | 80 | 160 | *320* | 80 | 40 | < | < | < | < |
| 4. A/Victoria/3/75 | 80 | 160 | 320 | *640* | 160 | 40 | 160 | 160 | < |
| 5. A/Texas/1/77 | < | 40 | 160 | 160 | *1280* | 320 | 320 | 320 | 160 |
| 6. A/Bangkok/1/79 | 320 | 80 | 320 | 320 | 1280 | *2560* | 1280 | 640 | 160 |
| 7. A/Philippines/2/82 | < | < | < | < | 80 | 40 | *320* | 160 | 80 |
| 8. A/Mississippi/1/85 | < | < | 80 | 40 | 160 | 160 | 320 | *640* | 320 |
| 9. A/Leningrad/360/86 | < | < | < | < | 80 | 20 | 320 | 320 | *640* |

< = less than 20
Homologous titers indicated in shaded boxes

The immune response to variants within a subtype depends upon the prior experience of the host. In unprimed children, natural infection induces predominantly antibodies specific to the infecting strain (Oxford, J. S., et al., 1981). In contrast, infected adults, previously exposed to an earlier subtype variant, produce predominantly cross-reacting and variant-specific antibody to that earlier variant as well as variant specific antibody to the infecting virus (Oxford, J. S., et al., 1979). In essence, a "broader" immune response is achieved.

The observation that antibodies induced by infection with influenza are primarily directed toward those determinants shared between viruses, is called "original antigenic sin". (Francis, T. Jr., et al., 1953). This phenomenon is a selective anamnestic response during influenza infection where the immunologic response is skewed toward the antigens experienced during the original infection. This probably occurs because multiple antibody combining sites exist on both the HA and NA, and sequential subtype variants arising during antigenic drift have amino acid changes in only one or two of them. Each new drift variant of epidemiological importance has generally had four or more amino acid substitutions located in two or more of the antigenic sites (Wiley D. C., et al., 1981).

Furthermore, the intravirion immunodominance of HA (see Antigenic Dominance, below) in the continuing competition between the two proteins reduces the immune response (and therefore selection pressure) against the NA. It is worth noting that with the influenza A viruses contains only 9 NA subtypes, but 14 HA subtypes have evolved through the years.

Since resistance to infection correlates with serum anti-HA antibody levels (Dowdle, W. R., et al., 1973; Couch, R. B. et al., 1983) the antigenic structure of the HA is of primary importance in strain selection for inclusion in the influenza vaccine each year. Resistance can also be correlated with local neutralizing antibody and secretory IgA antibody to HA as well as serum anti-HA antibody (Clements, M. L., et al., 1986). The relative importance of local or serum antibody in preventing influenza is still unknown.

Naturally acquired antibody to NA has also been correlated with resistance to challenge or natural infection (Kilbourne, E. D., et al. 1987; Kim, W., et al., 1976). Anti-NA antibody has been attributed with reducing the severity of clinical disease and contributing to the prevention of epidemic spread in man (Murphy, R. R. et al., 1972). Murphy, et al. concluded that "efforts should be made to stimulate NA antibody as well as antihemagglutinin antibody for more effective prophylaxis of influenzal disease". This is supported by the observation that virus infections occurring in Tecumseh in 1968–69, caused by the newly emerged A/Hong Kong/68 (H3N2) virus against which the population had no specific antibody to the HA, was significantly less frequent in subject with anti-NA antibody acquired by prior infection with the preceding influenza A (H2N2) viruses than in those without antibody to NA (Potter, C. W., et al., 1977; Gill, P. W., et al., 1971).

The influenza A virus two major surface glycoproteins, hemagglutinin (HA) and neuraminidase (NA), are highly immunogenic and are subject to continuous and sequential evolution within immune or partially immune populations. When NA is present in immunogenic form in the vaccine or on the intact virion, it is a minority component and therefore subservient to continuing antigenic competition with the immunodominant HA. However, it has now been surprisingly found this antigenic competition can be wholly or substantially eliminated by presenting the HA and NA as separate purified proteins.

The antibody induced by HA directly neutralizes virus infectivity; antibody to NA, while not neutralizing, limits viral replication in a multi-cycle infection and can reduce viral replication below a pathogenic threshold. However NA can synergistically enhance HA, when the NA is presented in sufficient quantity.

In addition, influenza A in particular can escape the prevalent immunity due to the phenomenon of "shift". In 1957 the NA1-type virus prevalent up to that time was thus replaced by a new NA2-type virus. Since 1977, the NA1-type viruses have also returned to the human population.

On account of their external localization, the HA and NA antigens represent the most important viral target structures for the host immune system. Of antibodies which bind specifically to HA, it is thought that they neutralize the viral infectivity, probably by blocking the early steps of infection (Hirst, 1942; Kida et al., 1983). NA-specific antibodies normally do not prevent the initial infection of a target cell (Jahiel and Kilbourne, 1966; Kilbourne et al., 1968; Johanssen et al., 1988). In addition, due to competitive mechanisms, the immunogenic response to NA appears to be partly suppressed in favor of the more frequently occurring HA antigen (Johanssen et al., 1987; Kilbourne, 1976). As a net result, the effect of NA immunity is generally overshadowed by the neutralizing HA antibodies. For this reason, the attention of vaccine designers has been focused for a long time almost exclusively on HA.

Seed viruses for influenza A and B vaccines are naturally occurring strains that replicate to high titers in the allantoic cavity of chicken eggs. Alternatively, the strain for the influenza A component is a reassortant virus with correct surface antigen genes. A reassortant virus is one that, due to segmentation of the viral genome, has characteristics of each parental strain. When more than one influenza viral strain infects a cell, these viral segments mix to create progeny virion containing various assortments of genes from both parents.

Protection with current whole or split influenza vaccines is short-lived and wanes as antigenic drift occurs in epidemic strains of influenza.

The current trivalent, hemagglutinin (HA) based vaccine is considered a generic product. Vaccination of primed young adults produces protective levels of anti-HA antibody in up to 90% of the vaccines (Quinnan, et al., 1983). The protective efficacy is high and commonly quoted at 60% to 80%, with the lower value seen after challenge with an antigenically drifted virus and the higher value seen when the virus causing disease is closely related to the vaccine virus (Dowdle, W. R. 1981; Ada, G., et al., 1987). In older age groups, this vaccine is less effective in preventing infection (Quinnan, G. V., et al. 1983). but remains effective (75%) in preventing complications and death following influenza infection. (Patriarca, P. A., et al., 1987; Barker, W. H. et al., 1980).

Influenza virus types A and B are characterized as enveloped viruses that contain an 8 segmented, negative strand RNA genome (Lamb, R. A. et al., 1983). Coding functions for mRNA and protein have been mapped to these individual segments by at least three methods. The virions are pleomorphic, with laboratory-adapted strains assuming a spherical shape with a diameter of 80 to 120 nm, while freshly isolated viruses are often filamentous. The virus envelope, derived from the host-cell membrane, is modified by insertion of two virus-coded glycoprotein spikes, the hemagglutinin (HA) and neuraminidase (NA) proteins. Both glycoproteins are anchored in the envelope by membrane-spanning regions of hydrophobic amino acids and the ratio of HA to NA in virions averages 5 to 1. The matrix (M1) protein forms an electron dense-layer immediately inside the host-derived membrane. Within the matrix shell are the nucleoprotein (NP) and polymerase proteins (PB1, PB2, and PA) which are closely associated with the single-stranded and segmented RNA genome of the virus. Collectively these structures are called the ribonucleoprotein (RNP) complexes which have RNA-dependent RNA polymerase (transcriptase) activity. The envelope of type A influenza (but not type B viruses) also contains one minor component, the M2 protein, which is coded for by the M protein RNA segment. The M2 protein functions as an ion channel that plays a role in uncoating the virus (Sugrue, R. J. et al., 1991).

Hemagglutinin (HA) initiates infection by binding to sialic acid receptors on the cell surface and mediating fusion between viral and endosomal membranes (Weis, W., et al., 1988; Skehel, J. J. et al., 1982). HA is so-named because of its role in the agglutination of erythrocytes (RBC), a reaction that has been exploited to study the antigenic nature of the molecule and the immune response to the HA. Antibody to the HA neutralizes virus infectivity (Virelizier, J. L., 1975) and thus provides the major selective pressure for the emergency of mutant viruses with epidemic potential (Palese, P. et al., 1982). The 3-D structure of the HA is known from X-ray crystallography and the location of the receptor binding site and the five antigenic sites of HA have been mapped to this structure. The antigenic sites were identified from amino acid sequence changes in naturally occurring variants as well as variants selected with monoclonal antibodies. The potency of current influenza vaccines is defined by single radial immunodiffusion (SRID) testing for HA antigen content. Influenza vaccines must be updated often as a consequence of antigenic drift of the HA molecule in circulating strains.

The hemagglutinin may also be isolated after treatment of the virions with a protease such as bromelain, then purified by a method such as that described by Grand and Skehel, Nature, New Biology, Vol. 238, 145–147, 1972.

HA and NA evolve quite differently. For example, the rate of silent nucleotide substitution has been shown to be higher than the rate of coding nucleotide substitutions for all genes of influenza virus, including the gene for HA (Reviewed by Webster et al.; Webster, R. G., et al., 1992). However, HA has a much higher rate of coding changes than the internal proteins. The elevated rate of coding nucleotide changes in the HA gene as compared with other genes has been taken as evidence that immune selection is an important factor in its evolution (Palese, P., et al., 1982). Using reasserted antigens to eliminate any nonspecific steric hindrance, Kilbourne et al. studied the rate of evolution of epidemiologically important HA and NA antigens isolated from humans over a 10-year period and determined that the HA evolved more rapidly than the neuraminidase (NA) (Kilbourne, E. D., et al., 1990). This was shown with both type A H1N1 and H3N2 viruses and has been confirmed by subsequent experiments with more recent strains. The reason for the apparently different rates of evolution is unknown but may be due to the fact that antibody to HA neutralizes virus and prevents infection. This places more selective pressure on the HA to maintain itself in a partially immune population.

Antibodies to HA neutralize the virus and form the basis for natural immunity to infection by influenza (Clements, 1992). Antigenic variation in the HA molecule is responsible for frequent outbreaks to influenza and for limited control of infection by immunization.

The three-dimensional structure of HA and the interaction with its cellular receptor, sialic acid, has been extensively studied (Wilson, et al. 1981; Weiss et al.; Murphy and Webster, 1990). The HA molecule is present in the virion as a tri-mer. Each monomer exists as two chains, HA1 and HA2, linked by a single disulfide bond. Infected host cells produce a precursor glycosylated polypeptide (HAO) with a molecular weight of about 85,000, which is subsequently cleaved into HA1 and HA2.

The presence of influenza HA-specific neutralizing IgG and IgA antibodies are associated with resistance to infection and illness (Clements, 1992). Inactivated whole virus or partially purified (split subunit) influenza vaccines are standardized to the quantity of HA from each strain. Influenza vaccines usually can include 7 to 25 micrograms HA from each of three strains of influenza.

On the other hand, NA catalyses the removal of terminal sialic acid residues of glycosyl groups whereby potential receptors for HA are destroyed (Gottschalk 1957; Burnet and Stone, 1947). It is assumed that NA is essential: in preventing virus aggregation; and, in an efficient spreading from cell to cell (Colman and Ward 1985).

Each NA molecule (Mw=240,000) has a toadstool-like structure which consists of four identical polypeptide chains built up of two dimmers which are linked to disulfide bridges and in turn held together by non-covalent bonds (Bucher and Kilbourne, 1972; Laver and Valentine, 1969; Varghese et al., 1983; Ward et al., 1983). In addition, NA is anchored in the lipid membrane by a non-spliced NA-terminal, lipophilic sequence (Fields et al., 1983; Block et al; 1982), the so-called membrane anchor. The greatest part of the total structure protrudes above the membrane and forms a distal, box-shaped "head" area localized on top of an elongate "stalk" region (Wrigley et al., 1973). Inside the head each monomer has its own catalytic site and contains at least four NA-linked glycosyl groups (Colman et al., 1983; Ward et al., 1982). The presence of O-glycosylation has not yet been demonstrated up to the present time.

Sequence determination of antigenic variants, produced by growing virus in the presence of high concentrations of antibody to the NA, indicate that single amino acid changes occur that are located at the top of the molecule on the rim around the active site of the enzyme (Air, G. M., et al., 1985). This suggest that NA inhibiting epitopes are located in this area. Liu et al. (Liu, C., et al., 1995) have shown that a neuraminidase-deficient influenza virus was capable of entry, replication, and assembly while virus particles were not released. Therefore, NA appears to release newly assembled virus particles from the cell surface. (Palese, P., et al., 1974). Thus, the NA performs a late function in the influenza a replication cycle, whereas the HA performs an early, initial functions of binding and fusion required for infection.

A number of experimental observations indicate however that NA is indeed capable of playing a significant part in the build-up of protective immunity to influenza (Schulman et al., 1968; Johanssen and Kilbourne, 1990; Johansen et al., 1993). Up to now, NA was prepared by treating viral envelopes with detergents (Gallagher et al., 1984; Kilbourne et al., 1968) or by proteolytic cleavage of the protein head, often by means of pronase (Seto et al., 1966; Rolt et al., 1974), followed by purification of the NA. Thus, it is within the ambit of the skilled artisan to prepare NA for use in this invention. Recombinant NA or NA from in vivo expression of NA from coding DNA, RNA or a vector containing either coding DNA or RNA, are available by means known to the skilled artisan. PCT published application, WO 95/18861 published Jul. 13, 1995, is hereby incorporated by reference.

The influenza vaccine of the invention therefore also can be an anti-influenza vaccine additionally containing NA wherein the NA is recombinant neuraminidase or NA from in vivo expression.

In vitro techniques have established that NA antibodies can efficiently suppress the yield of virus growth by inhibiting the release and spread of virus particles (Jahiel and Kilbourne, 1968; Kilbourne et al., 1968). Similar conclusions were drawn from animals immunized with NA by measuring decreased virus titres in the lungs and reduced development of lung lesions. However, NA antibodies are not neutralizing; and, it is surprising that NA added in sufficient quantity to an otherwise conventional anti-influenza vaccine enhances efficacy, and provides enhanced cross-protection.

Although considerable attention has been devoted to the effect of the NA immunity on virus replication in the lungs, it was questionable whether immunization with pure NA protein could prevent clinical disease symptoms or could improve the chances of survival after a potentially lethal influenza infection. No satisfactory answer has as yet been provided to this question. The results shown herein clearly demonstrate however that enhanced protection against influenza infection can be achieved by immunization with an anti-influenza vaccine containing NA as an additive.

Less information is available on the changes in sequences of NA proteins, although limited data suggest, also, a more rapid rate of change of the NA than is seen with the internal proteins. However, the evolutionary rate of HA and NA antigenic phenotypes as the reciprocal of immunological selection may, without wishing to be bound by any one theory, provide a basis for enhanced efficacy and enhanced cross-protection observed in the present invention; but, heretofore, it is believed, that exploiting the rate of antigenic phenotypes as the reciprocal of immunological Selection of NA and HA has not been taught or suggested.

Antibody to the NA does not prevent infection but reduces virus yield by inhibiting virus release. Therefore, the NA might be expected to incur less direct selective pressure in the face of antibody.

However, since an experimental vaccine based on neuraminidase antigen was previously found to be only partially protective in a human trial (Ogra et al., J. Infect. Dis. 135499–506 (1977)), this is evidence that the present invention is novel and nonobvious, since the enhanced efficacy and cross protection the present invention provides is therefore a surprising and unexpected result.

The data herein provides that an NA supplemented standard influenza vaccine of the present invention would increase vaccine effectiveness in two ways. The inventive vaccine prevents infection by inhibiting the HA function with added effects of homologous NA inhibition when a good HA match and an adequate immune response to the HA occurs. The greatest benefit occurs when the HA of the epidemic strain evolved from that contained in the vaccine or where an adequate immune response to the HA has not occurred, and a mild, immunizing infection would occur. This infection would be reduced in severity by the antibody response to the supplemented NA but the individual nonetheless, is immunized to the newly emergent HA due to the infection. The outcome of various scenarios are summarized in Table form below.

Predicted Outcomes Following Administration of Various Vaccine Formulations and Hypothetical Epidemic Virus Subvariant (HA$_1$, HA$_2$, HA$_3$) Scenarios

| *Vaccine strain HA | *Epidemic strain HA | Protection from Infection | Protection from Disease | Reduced Virus Shedding | #Protection from Epidemic Virus, HA$_3$ |
|---|---|---|---|---|---|
| HA$_1$ | HA$_1$ | yes | yes | yes | no |
| HA$_1$ | HA$_2$ | no | no | no | no |
| HA$_1$ + NA | HA$_1$ | yes | yes | yes | partial |
| HA$_1$ + NA | HA$_2$ | no | yes | yes | partial |

*Scenario assumes similar NA in vaccine and epidemic virus strains
HA3 virus encountered in the following influenza season The fact that the NA undergoes more gradual antigenic drift as compared with HA makes the approach of the present invention attractive and feasible. Another clear advantage of the present invention is that it places less absolute importance on the exact match of the HA antigen in the vaccine and the epidemic strain, a decision that must be made eight months before the target season.

Finally, the presentation in the supplemented vaccine of the present invention of purified NA in a form not physically associated with the HA, prevents or lessens HA immunodominance (seen with standard vaccines).

While the HA and NA are immunogenic proteins in animals and humans, NA immunogenicity is influenced by the HA when presented to the immune system on the same virion particle. In comparisons of the NA response with H3N2 and H7N2 antigenic hybrid inactivated viruses, Kilbourne (Kilbourne, E. D., 1976) observed that only 25% of the people responded to NA in the conventional H3N2 particle whereas 69% responded to the NA in the H7N2 vaccine. Subsequent studies revealed that when presented on the same particle, HA is immunogenically dominant over NA in a population primed to that HA and that this occurred in B- and T-cell priming (Johansson, B. E., et al., 1987).

It was observed that when the HA and NA are dissociated from virus and purified, they are immunogenically equivalent and no antigenic competition occurred between the purified molecules (Johansson, B. E., et al., 1989; Johansson, B. E. et al., 1993). Moreover, a mixture of purified NA molecules (N1 and N2), a prerequisite for any vaccine candidate, indicated that no competition between N1 and N2 occurred in primary or secondary immune responses in mice (Johansson, B. E. et al., 1994). Thus, NA, as according to the present invention can be from one or different strains, i.e., the invention need not be limited to exemplified NA, and the NA additive can be from one or more strains.

The vaccine according to the invention can also provide protection against still further removed drift variants. By means of genetic modification of the NA gene, variations can be made in the antigenic structure thereof. It thus is possible to prepare "cocktails" of different versions of the NA, whereby extensive protection against different influenza strains can be obtained. Thus the invention comprehends NA "cocktail" as an additive; the "cocktail" being from admixture of NAs from various strains, and/or admixture of different versions of NA.

Antibody to either HA or NA has been correlated with protection from influenza albeit by different mechanisms of inhibition of viral replication. Since the NA content is uncontrolled in current influenza vaccines and both NA and HA are present in circulating influenza strains, the relative contributions of anti-NA antibody to protection is unknown. In light of evidence that anti-NA alone may dampen influenza disease, a rational approach to vaccine formulation should take advantage of protective mechanisms generated by both anti-HA and anti-NA antibody. Therefore, the present invention provides supplementing influenza vaccine with defined levels of purified NA to take advantage of the benefit of anti-NA antibody in combination with anti-HA antibody.

In the composition of the present invention, the first and second constituents, that is the conventional vaccine and the additive, may be put together in the same container. They may also be present in separate containers placed in the same wrapping, with a view to mixing them on use or administering them separately.

The composition of the present invention may contain the first and second constituents, combined or separated, suspended in a suitable liquid vehicle.

The two constituents of the vaccine composition of the present invention, whether together or separate, may also be presented in a freeze-dried form. The liquid composition is then reconstituted by mixing the composition with a usual liquid vehicle, at the time of using.

The composition of the present invention is generally presented in a form of an individual vaccine dose (unit dose), constituted either by a vaccinating-unit dose of the two constituents mixed, or by a unit dose of conventional vaccine, and a unit dose of N/A.

Dosages for humans or other mammals can be determined without undue experimentation by the skilled artisan, from the Examples below and the discussion herein, when considered in light of the knowledge in the art.

Sequence determination of antigenic variants, produced by growing virus in the presence of high concentrations of antibody to the NA, indicate that single amino acid changes occur that are located at the top of the molecule on the rim around the active site of the enzyme (Air, G. M., et al., 1985). This suggest that NA inhibiting epitopes are located in this area. Liu et al. (Liu, C., et al., 1995) have shown that a neuraminidase-deficient influenza virus was capable of entry, replication, and assembly while virus particles were not released. Therefore, NA appears to release newly assembled virus particles from the cell surface. (Palese, P., et al. 1974). Thus, the NA performs a late function in the influenza a replication cycle, whereas the HA performs an early, initial functions of binding and fusion required for infection.

A vector or recombinant for in vivo or in vitro expression of NA and/or HA or an epitope of interest thereof for use in the invention can be any suitable vector such as a bacterial, virus, or plasmid or naked DNA vector.

The methods for making a vector or recombinant for in vivo expression, e.g., of HA and/or NA (and thus including the vector or recombinant in the inventive composition) or for in vitro expression, e.g., of HA and/or NA (and thus including an expression product of the vector in the inventive composition) can be by or analogous to the methods disclosed in U.S. Pat. Nos. 4,603,112, 4,769,330, 5,174,993, 5,505,941, 5,338,683, 5,494,807, 4,722,848, Paoletti, "Applications of pox virus vectors to vaccination: An update," PNAS USA 93:11349–11353, Oct. 1996, Moss, "Genetically engineered poxviruses for recombinant gene expression, vaccination, and safety," PNAS USA 93:11341–11348, October 1996, Smith et al., U.S. Pat. No. 4,745,051 (recombinant baculovirus), PCT patent publication PCT/US95/06750, WO 96/37624, Richardson, C. D. (Editor), *Methods in Molecular Biology* 39, "Baculovirus Expression Protocols" (1995 Humana Press Inc.), Smith et al., "Production of Huma Beta Interferon in Insect Cells Infected with a Baculovirus Expression Vector," Molecular and Cellular Biology, Dec., 1983, Vol. 3, No. 12, p. 2156–2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 399–406; EPA 0 370 573, U.S. application Ser. No. 920,197, filed Oct. 16, 1986, EP Patent publication No. 265785, U.S. Pat. No. 4,769,331 (recombinant herpesvirus), Roizman, "The function of herpes simplex virus genes: A primer for genetic engineering of novel vectors," PNAS USA 93:11307–11312, October 1996, Andreansky et al., "The application of genetically engineered herpes simplex viruses to the treatment of experimental brain tumors," PNAS USA 93:11313–11318, October 1996, Robertson et al. "Epstein-Barr virus vectors for gene delivery to B lymphocytes," PNAS USA 93:11334–11340, October 1996, Frolov et al., "Alphavirus-based expression vectors: Strategies and applications," PNAS USA 93:11371–11377, October 1996, Kitson et al., J. Virol. 65, 3068–3075, 1991; U.S. Pat. Nos. 5,591,439, 5,552,143, Grunhaus et al., 1992, "Adenovirus as cloning vectors," Seminars in Virology (Vol. 3) p. 237–52, 1993, Ballay et al. EMBO Journal, vol. 4, p. 3861–65, Graham, Tibtech 8, 85–87, April, 1990, Prevec et al., J. Gen Virol. 70, 429–434, PCT WO91/11525, Felgner et al. (1994), J. Biol. Chem. 269, 2550–2561, Science, 259:1745–49, 1993 and McClements et al., "Immunization with DNA vaccines encoding glycoprotein D or glycoprotein B, alone or in combination, induces protective immunity in animal models of herpes simplex virus-2 disease," PNAS USA 93:11414–11420, October 1996, and U.S. Pat. Nos. 5,591, 639, 5,589,466, and 5,580,859 relating to DNA expression vectors, inter alia; each of which is incorporated herein by reference.

Techniques for engineering recombinant or vector subunit compositions are known in the art. With respect to techniques for these immunization vehicles and state-of-the-art knowledge, mention is particularly made of: Hormaeche and Kahn, Perkus and Paoletti, Shiver et al. all in *Concepts in Vaccine Development*, Kaufman, S. H. E., ed., Walter deGruytes, New York, 1996, and vectors described in *Viruses in Human Gene Therapy*, Vos, J.-M. H., ed, Chapman and Hall, Carolina Academic Press, New York, 1995, and in *Recombinant Vectors in Vaccine Development*, Brown, F., ed., Karger, New York, 1994.

Techniques for protein purification of native or recombinant proteins, in general, are as follows:

Briefly, the cells are disrupted and the protein of interest is released into an aqueous "extract". There are many methods of cellular disintegration, which vary from relatively gentle to vigorous conditions, and the choice of one method over the other is dependent upon the source material. Animal tissues vary from the very easily broken erythrocytes to tough collagenous material such as found in blood vessels and other smooth-muscle containing tissue. Bacteria vary from fairly fragile organisms that can be broken up by digestive enzymes or osmotic shock to more resilient species with thick cell walls, needing vigorous mechanical treatment for disintegration.

Gentle techniques include cell lysis, enzymatic digestion, chemical solubilization, hand homogenization and mincing (or grinding); moderate techniques of cell disintegration include blade homogenization and grinding with abrasive materials, i.e., sand or alumina; and vigorous techniques include french press, ultrasonication, bead mill or Manton-Gaulin homogenization. Each of the aforementioned techniques are art-recognized, and it is well within the scope of knowledge of the skilled artisan to determine the appropriate method of cell disintegration based upon the starting material, and the teachings herein and in the art.

Following cell disintegration, the extract is prepared by centrifuging off insoluble material. At this stage, one may proceed with the purification method, as an extract containing as much of the protein of interest as possible has been prepared, and, where appropriate, particulate and most non-protein materials have been removed.

Standard techniques of protein purification may be employed to further purify the protein of interest, including: precipitation by taking advantage of the solubility of the protein of interest at varying salt concentrations, precipitation with organic solvents, polymers and other materials, affinity precipitation and selective denaturation; column chromatography, including high performance liquid chromatography (HPLC), ion-exchange, affinity, immuno affinity or dye-ligand chromatography; immunoprecipitation and the use of gel filtration, electrophoretic methods, ultrafiltration and isoelectric focusing. Each of the above-identified methods are well within the knowledge of the skilled artisan, and no undue experimentation is required to purify the native proteins or epitopes of interest of NA, using the standard methodologies outlined hereinabove, and in the literature, as well as the teachings herein.

For information on NA, natural or recombinant, and isolation and/or purification thereof, reference is made to WO 95/18861, WO 94/11005, CA 2081068, WO 93/06218, WO 92/06691, WO 91/05055, WO 89/11534, Ogra et al., J.

Infect. Dis. 135:499–506 (1977), Johansson et al., J. Virology, 63:1239–1246 (1989), each incorporated herein by reference.

As indicated, the NA in inventive compositions need not necessarily be whole NA, but rather can be an epitope or epitopes of interest of NA (and if more than one epitope is present, it they may be present as individual molecules, or as epitopes conjugated to each other, or as epitopes otherwise chemically linked (e.g., covalently or ionically) to each other to form a single chemical moiety). As to epitopes of interest, one skilled in the art can determine an epitope or immunodominant region of a peptide or polypeptide and ergo the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

A general method for determining which portions of NA to use in an immunological or vaccine composition focuses on the size and sequence of the NA or portion thereof of interest. "In general, large proteins, because they have more potential determinants are better antigens than small ones. The more foreign an antigen, that is the less similar to self configurations which induce tolerance, the more effective it is in provoking an immune response." Ivan Roitt, *Essential Immunology*, 1988.

As to size: the skilled artisan can maximize the size of the protein encoded by the DNA sequence to be inserted into the mammalian vector (keeping in mind the insertion limitations of the vector). To minimize the DNA inserted while maximizing the size of the protein expressed, the DNA sequence can exclude introns (regions of a gene which are transcribed but which are subsequently excised from the primary RNA transcript).

At a minimum, the DNA sequence can code for a peptide at least 8 or 9 amino acids long. This is the minimum length that a peptide needs to be in order to stimulate a CD4+T cell response (which recognizes virus infected cells or cancerous cells). A minimum peptide length of 13 to 25 amino acids is useful to stimulate a CD8+T cell response (which recognizes special antigen presenting cells which have engulfed the pathogen). See Kendrew, *The Encyclopedia of Molecular Biology* (Blackwell Science Ltd. 1995). However, as these are minimum lengths, these peptides are likely to generate an immunological response, i.e., an antibody or T cell response; but, for a protective response (as from a vaccine composition), a longer peptide is preferred.

With respect to the sequence, the DNA sequence preferably encodes at least regions of the peptide that generate an antibody response or a T cell response. One method to determine T and B cell epitopes involves epitope mapping. The protein of interest "is fragmented into overlapping peptides with proteolytic enzymes. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules. The method is less effective for determining B-cell epitopes" since B cell epitopes are often not linear amino acid sequence but rather result from the tertiary structure of the folded three dimensional protein. Janis Kuby, *Immunology*, pp. 79–80 (1992).

Another method for determining an epitope of interest is to choose the regions of the protein that are hydrophilic. Hydrophilic residues are often on the surface of the protein and are therefore often the regions of the protein which are accessible to the antibody. Janis Kuby, *Immunology*, p. 81(1992).

Yet another method for determining an epitope of interest is to perform an X-ray crystallographic analysis of the antigen (full length)-antibody complex. Janis Kuby, *Immunology*, p. 80 (1992).

Still another method for choosing an epitope of interest which can generate a T cell response is to identify from the protein sequence potential HLA anchor binding motifs which are peptide sequences which are known to be likely to bind to the MHC molecule.

The peptide which is a putative epitope of interest, to generate a T cell response, should be presented in a MHC complex. The peptide preferably contains appropriate anchor motifs for binding to the MHC molecules, and should bind with high enough affinity to generate an immune response. Factors which can be considered are: the HLA type of the patient expected to be immunized, the sequence of the protein, the presence of appropriate anchor motifs and the occurrence of the peptide sequence in other vital cells.

An immune response is generated, in general, as follows: T cells recognize proteins only when the protein has been cleaved into smaller peptides and is presented in a complex called the "major histocompatibility complex MHC" located on another cell's surface. There are two classes of MHC complexes—class I and class II, and each class is made up of many different alleles. Different patients have different types of MHC complex alleles; they are said to have a "different HLA type".

Class I MHC complexes are found on virtually every cell and present peptides from proteins produced inside the cell. Thus, Class I MHC complexes are useful for killing cells which when infected by viruses or which have become cancerous and as the result of expression of an oncogene. T cells which have a protein called CD8 on their surface, bind specifically to the MHC class I/peptide complexes via the T cell receptor. This leads to cytolytic effector activities.

Class II MHC complexes are found only on antigen-presenting cells and are used to present peptides from circulating pathogens which have been endocytosed by the antigen-presenting cells. T cells which have a protein called CD4 bind to the MHC class II/peptide complexes via the T cell receptor. This leads to the synthesis of specific cytokines which stimulate an immune response.

Some guidelines in determining whether a protein contains epitopes of interest which will stimulate a T cell response, include: Peptide length—the peptide should be at least 8 or 9 amino acids long to fit into the MHC class I complex and at least 13–25 amino acids long to fit into a class II MHC complex. This length is a minimum for the peptide to bind to the MHC complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia, M. et al., *Specific Binding of Leukemia Oncogene Fusion Protein Peptides to HLA Class I Molecules,* Blood 85:2680–2684; Englehard, V H, *Structure of peptides associated with class I and class II MHC molecules* Ann. Rev. Immunol. 12:181 (1994)). This can be done, without undue experimentation, by comparing the sequence of the protein of interest with published structures of peptides associated with the MHC molecules. Protein epitopes recognized by T cell receptors are peptides generated by enzymatic degradation of the protein molecule and are presented on the cell surface in association with class I or class II MHC molecules.

Further, the skilled artisan can ascertain an epitope of interest by comparing the protein sequence with sequences listed in the protein data base. Regions of the protein which share little or no homology may, in some instances, be better choices for being an epitope of that protein and can therefore be useful in a vaccine or immunological composition. Regions which share great homology with widely found sequences present in vital cells, in some instances, may be less useful.

Even further, another method is simply to generate or express portions of a protein of interest, generate monoclonal antibodies to those portions of the protein of interest, and then ascertain whether those antibodies inhibit growth in vitro of the pathogen from which the protein was derived. The skilled artisan can use the other guidelines set forth in this disclosure and in the art for generating or expressing portions of a protein of interest for analysis as to whether antibodies thereto inhibit growth in vitro.

For example, the skilled artisan can generate portions of a protein of interest by: selecting 8 to 9 or 13 to 25 amino acid length portions of the protein, selecting hydrophilic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid and corresponding DNA sequence of a NA epitope of interest for obtaining a T cell, B cell and/or antibody response. In addition, reference is made to Gefter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing antibodies are directed. Disclosures of such epitopes are in many of the references cited in the Relevant Literature section.")

Glycosylation of NA may be important for immunogenicity; so, it may be important to maintain a proper level of glycosylation, e.g., avoid removal or denaturation when isolating and/or purifying native or recombinant NA or an epitope thereof, avoid recombinant expression with hyperglycosylation, avoid recombinant expression without glycosylation or with insufficient glycosylation, etc.

Especially preferred are vaccine compositions which comprise an anti-influenza vaccine, having as an additive, a substantially pure, recombinant influenza neuraminidase protein, wherein said protein is purified to about 90% or greater. Also especially preferred is a vaccine composition which comprises a substantially pure, recombinant, mature, glycosylated influenza hemagglutinin protein, wherein the protein is purified to about 90% or greater and said protein is immunogenic and induces a protective immune response when used as a vaccine and a substantially pure, recombinant influenza neuraminidase protein, wherein said protein is purified to about 90% or greater. An especially preferred protein is that produced by a baculovirus expression system in cultured insect cells.

Examples of NA-supplemented compositions of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and preparations for parenteral, subcutaneous, intradermal, intramuscular or intravenous administration (e.g., injectable administration), such as sterile suspensions or emulsions. The choice of a composition can be determined by whether a local or systemic response is desired, as preparations for parenteral, subcutaneous, intradermal, intramuscular or intravenous administration may induce a systemic response, whereas compositions for orifice or mucosal administration may induce a local response. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, Ph buffering agents, gelling or viscosity enhancing additives, preservatives, flavoring agents, colors, and the like, depending upon the route administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected Ph. If digestive tract absorption is preferred, compositions of the invention can be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or, a dose having a particular particle size.

Liquid preparations are normally easier to prepare than gels, viscous compositions, and solid compositions.

Additionally, liquid compositions are somewhat more convenient to administer, especially by injection or orally, to animals, children, particularly small children, and others who may have difficulty swallowing a pill, tablet, capsule or the like, or in multi-dose situations. Viscous compositions, on the other hand, can be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the antigens, and optional adjuvant. Minor amounts of other ingredients such as Ph adjusters (e.g., a base such as NaOH), emulsifiers or dispersing agents, buffering agents, preservative, wetting agents, jelling agents, (e.g., methylcellulose), colors and/or flavors may also be present. The inventive compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

As can be appreciated from the presently conventional manner of administering anti-influenza vaccines, and from the Examples below, compositions of the invention are preferably formulated for administration by injection. However, given that influenza does affect the respiratory tract, other means of administration and formulations therefor, are not necessary excluded from the invention.

Formulations can be inhalables, e.g., sprays and the like. Aerosol spray preparations can be in a pressurized container with a suitable propellant such as a hydrocarbon propellant. Pump spray dispensers are commercially available, e.g., from Valois of America, Inc., Connecticut. Nasal spray dispensers are commonly fabricated from a flexible material such as plastic and cause a spray to dispense in response to being squeezed. Anti-inflammatories, such as "Vanceril" are commercially available in oral and nasal aerosol form for mucosae administration; the anti-inflammatory "Vancerase" is commercially available in a pump-spray dispenser for nasal administrations; cold remedies such as "Dristan" are commercially available in nasal spray (squeeze) dispensers (so that the reader is aware that aerosol, pump and squeeze dispensers are known and available).

The inventive NA-supplemented vaccine composition may be formulated in any convenient manner and in a dosage formulation consistent with the mode of administration and the elicitation of a protective response. The quantity of antigen or epitope of interest to be administered depends on the subject to be immunized. Suitable dosage ranges, however, are readily determinable by those skilled in the art and may be of the order of micrograms to milligrams, e.g., 5 to 500 ug of NA and 5 to 500 ug of HA in inventive compositions. Suitable regimes for initial administration and booster doses also are variable, but may include an initial administration followed by subsequent administration(s).

The therapeutically effective compositions of this invention are prepared by mixing the ingredients following generally accepted procedures. For example the selected components may be simply mixed in a blender, or other standard device to produce a concentrated mixture which may then be adjusted to the final concentration. Compositions can be administered in dosages and by techniques well known to those skilled in the medical arts taking into consideration such factors as the age, sex, weight, and condition of the particular patient, and the particular route of administration, intraperineal, intravenous, intravascular, intramuscular, subcutaneous, intradermal, intranasal, oral, peroral, mucosal, intragastic, etc.

The following Examples are given for illustration only and are not intended as a limitation of the invention.

EXAMPLES

Example 1

Doses of NA ranging from 2.6 to 69.6 μg of purified, non-adjuvanted NA in carrier (saline) were administered to human subjects aged 18–40 by the i.m. route. Comparisons were made to a conventional trivalent influenza vaccine. The safety of the vaccines was documented by the fact that the conventional vaccine and purified NA vaccine did not induce significant systemic reactions. Reactions at the site of injection were mild and associated with the conventional vaccine and the highest dose of NA vaccine.

Antibody responses to NA were measured by NA enzyme-inhibiting and NA-specific EIA tests. Peak antibody responses were observed two to three weeks after immunization and persisted for six months. The antibody responses were approximately equivalent to the dose of NA administered. The response to conventional vaccine was equivalent to approximately 7 μg of purified NA. Doses of 23 and 69 μg of purified NA gave superior antibody responses.

Example 2

The supplementation strategy of the present invention and testing thereof is quite straightforward. Briefly, animals were injected with various vaccine preparations, blood drawn at specified times and the sera assayed for antibodies against NA and HA. Then mice were challenged with a mouse-adapted influenza virus and the effect of this infectious challenge were assayed.

Mice were immunized with three doses of 1 μg Nas which were given in intervals of two weeks. Vaccinated animals were capable of totally surviving a lethal infection of influenza virus, wherein the virus expressed homo- or het- E. et al., 1987; Johansson, B. E. et al., 1990). These studies also demonstrated that purified NA is highly immunogenic without adjuvant and that immunogenicity is not altered by formalin treatment of the purified NA preparation.

Below are results of trial in mice of an A/Beijing/32/92 (H3N2) vaccine with and without an N2NA supplement. The results demonstrate the ability of an NA supplemented vaccine to attenuate illness in mice challenged with a heterologous virus to a greater degree than the conventional non-supplemented vaccine.

Attenuation of Influenza Infection in Mice with Influenza Vaccine Supplemented with Purified Neuraminidase

| Vaccine (day 0) | Vaccine Boost (day 30) | NI Antibody $\log_2$ (day 28 post Boost) | HI Antibody $\log_2$ (day 28 post Boost) | Lung Titer following Heterologous Challenge# |
|---|---|---|---|---|
| *H3N2 | £H3N2 | 4.0 | 3.2 | $3.6 \times 10^4$ pfu |
| **H3N2 + N2 | ££H3N2 + N2 | 8.0 | 3.8 | $3.8 \times 10^2$ pfu |
| PBS | — | — | — | $1.6 \times 10^6$ pfu |

*A/Beijing/32/92 commercial vaccine adjusted to contain 10 μg NA
**A/Beijing/32/92 commercial vaccine adjusted to contain 10 μg NA plus 10 μg purified NA
£/Beijing/32/92 commercial vaccine adjusted to contain 1 μg NA
££Beijing/32/92 commercial vaccine adjusted to contain 1 μg NA plus 1 μg purified NA
Mice challenged with A/Leningrad/360/86 (H3N2)

erovariant NA. In view of the high dose of infection virus it was very striking how well immunized animals remained free of clinical disease symptoms as indicated by changes in temperature and body weight. It is important to note that adjuvants were not administered with NAs, so that the immunization procedure described herein is directly applicable for human vaccination. The vaccines according to the invention are, in addition, relevant for animals other than humans, e.g., other vertebrates subject to influenza, such as other mammals and birds.

Passive transfer of serum of mice which were immunized with Nas to naive recipient mice resulted in the same levels of protection, which indicated that the protective effect of Nas immunization can be explained on the basis of circulating NA antibodies.

With regard to the heterovariant protection described herein, it is important to consider the structural relation between the NA antigen of the vaccine A/Victoria/3/75 and the NA of A/Aichi/2/68 which is present in the variant infection virus X-31. Unfortunately, no sequence data is available relating to the NA of A/Aichi/2/68 (H3N2), although a comparison can however be made with the NA sequence of A/NT/60/68 (H3N2) (Bentley and Brownlee, 1982), isolated in the same year as the Aichi strain. Examining closely the head region of both NA variants, amino acid substitutions are found at 28 positions, wherein the majority is located on the surface of the molecule.

Purified NA Animal Studies

A series of studies in Balb/c mice showed that highly purified NA induce a specific immune response to NA which, although infection-permissive, reduced pulmonary virus titers and lesions and lessens the systemic impact of infection as measured by loss in body weight (Johansson, B.

In this study (see Table 18 and Table 19), Applicants found: 1) NA-supplemented vaccine is highly NA immunogenic (compare Groups 4 and 1). 2) This enhanced NA response did not reduce the anti-HA immune response (compare Groups 2 & 3 to Group 4). When these animals were challenged with an influenza virus containing an HA antigenically distantly related (i.e., A/Leningrad/360/86) to the immunizing HA (A/Beijing/32/92), and due, it is believed (without necessarily wishing to be bound by anyone theory), to the slower NA antigenic evolution, an containing NA that was 50% antigenically related, a 4 $\log_{10}$ reduction in viral titer in lungs of mice immunized with either purified N2 (Group 1) or NA-supplemented vaccine (Group 4) was observed relative to unimmunized control animals (Group 5). 3) conventional H3N2 vaccine groups (i.e., Group 2 and 3) had only a modest 1 to 2 $\log_{10}$ reduction in pulmonary virus titers.

Encouraged by the above results, a more detailed study of the effect of NA-supplementation on influenza viral immunity and its effect on homotypic and heterovariant infectious challenge was conducted (see Tables 20 and 21). Again, animals were immunized with different vaccine preparations with the plan to challenge with infectious virus after immunization. A comparison of the data in Table 21 (see also Table 20) shows that as seen in the earlier results (Tables 18 and 19, below): 1) NA-supplanted vaccine has increased NA-immunogenicity compared with conventional vaccines and 2) no suppression of the HA immune response was observed.

Turning to the data summarized in Table 24 below, sera obtained from these animals were assayed in a tissue culture system. In this system HA-antibody causes plaque inhibition (i.e., fewer plaques), whereas antibody to the NA simply reduces the size of plaques (i.e., plaque size reduction). In order to assay plaque size reduction a tissue culture grown influenza virus was employed which contained an H6-HA, novel to these animals immunologic experience thereby circumventing the plaque inhibiting effects of HA-antibody. Table 24 (extracted from the more complicated summary of Table 23 below) demonstrates that the supplemented vaccine induces both plaque inhibiting (neutralizing) and plaque size reducing antibody in equal amounts, providing a balanced immune response (compare Group 3 to Groups 1 & 2). Finally, these mice were challenged either with an infectious homotypic virus (A/Johannesburg/33/94) or one of two heterovariant strains (A/Beijing/32/92 or A/Leningrad/360/86).

After infection, the lungs of the mice were removed and the amount of virus in each calculated using a tissue culture system (See, Tables 25 and 26, below). Table 26 shows that the homotypic infection of all vaccines were protective, including the purified NA-vaccine (Group 1) which had a 3 $\log_{10}$ reduction in pulmonary virus titer relative to unimmunized controls. Table 23 shows that the supplemented vaccine group (Group 5) may have an extended homotypic protection; compare the higher plaque size reduction titer using the H3N2 test virus compared to the H6N2 test virus. These data suggest that the two sets of antibody, to HA and NA which are now balanced in amount may be functioning in concert. Further experimentation is needed to confirm this finding. Heterotypic challenge, highlights the effectiveness of the supplemented vaccine. Again using the core data from Table 26, can be seen that supplemented (Group 3) and purified N2-NA (Group 1) vaccines had reduced pulmonary virus titers: 4 $\log_{10}$ reduction in the A/Beijing challenge and 1.5 to 2 log°10 reduction in the A/Leningrad challenge. Whereas, the conventional vaccine (Group 2) had only a 1.5 $\log_{10}$ reduction in virus titer and a 0.5 $\log_{10}$ reduction, in the A/Beijing and A/Leningrad groups, respectively. Applicants conclude that NA-supplemented vaccines of the invention induce an immunity that reduces viral replication in heterovariant viral challenge.

Example 3

Clinical trials: the vaccine formulation consists of trivalent split influenza vaccine (Tri-vac), Tri-vac supplemental with 15 μg or 45 μg of purified N2 NA, and 15 μg or 45 μg or purified N2 NA alone. The vaccines are delivered in 0.5 ml volumes.

The strategy for preparing the vaccine formulations for this trial is as follows. Starting material is standard manufacturing monovalent bulks. Tri-vac at 2×concentration in PBS is mixed with 4 Mm CaCl Buffer to make the final formulations. The monovalent NA vaccines are mixed with PBS to prepare the final formulations. Placebo consists of equal volumes of PBS and 4 Mm CaCl buffer. Results parallel those observed in model animals discussed above.

Example 4

Fluzone® Influenza Virus Vaccine, Trivalent ("Trivac"), is commercially available from Connaught Laboratories, Inc., Swiftwater, Pa. Purified NA is prepared in accordance with techniques known in the art, see, e.g., WO 95/18861, WO 94/11005, CA 2081068, WO 93/06218, WO 92/06691, WO 91/05055, WO 89/11534, Orga et al., J. Infect. Dis. 135:499–506 (1977), Johansson et al., J. Virology, 63:1239–1246 (1989), each incorporated herein by reference. Fluzone® and NA are admixed with about 1, 2.5, 5, 10, 15, or 30 ug of NA added to a conventional dose of Fluzone®.

Various data from these Examples and the foregoing Detailed Description are provided in the following Tables:

Table 1 below shows a summary in human trials of the NA antibody responses to NAV and Tri-vacc in ELISA tests.

TABLE 1

Summary of NA Antibody Responses to NAV and Tri-Vacc in ELISA Tests (Geometric Mean Titers)

| Group | NA Dose | 0 | 14 | 180 | Conversion | % |
|---|---|---|---|---|---|---|
| A | 2.6 μg | 13.33 | 13.96 | 13.84 | 3/20 | 15 |
| B | 7.7 μ | 13.55 | 14.56 | 14.30 | 5/20 | 25 |
| C | 23.2 μg | 13.58 | 15.74 | 14.72 | 15/20 | 75 |
| D | 69.6 μg | 13.24 | 16.04 | 14.91 | 16/20 | 80 |
| E | Tri-Vacc | 13.58 | 15.21 | 14.26 | 11/20 | 55 |

Table 2 below provides Na-antibody response data in human trials measured using $H7N2_{vic\ 75}$ virus.

TABLE 2

NI Antibody Response Measured with $H7N2_{Vic.75}$ Virus (Putative Priming Antigen)

| Group/Dose | Mean titer (log 2) 0 day | Mean titer (log 2) 21 day | Increase log 2 |
|---|---|---|---|
| A 2.6 μg | 4.7 (26)[1] | 5.7 (52) | 1.0 |
| B 7.7 μg | 5.3 (39) | 6.2 (74) | 0.9 |
| C 23.2 μg | 4.8 (28) | 7.1 (138) | 2.3 |
| D 69.6 μg | 4.1 (17) | 6.8 (112) | 2.7 |
| E Tri-Vacc | 4.6 (24) | 5.9 (60) | 1.3 |
| mean | 4.7[2] | | 1.7 |

[1]arithmetic titers in brackets
[2]not including group E

Table 3 below provides reactions after purified influenza virus neuraminidase vaccine with data on location and severity of symptoms in human trials.

TABLE 3

Reactions After Purified Influenza Virus Neuraminidase Vaccine

| | | Location and Severity of Symptoms | | | | |
|---|---|---|---|---|---|---|
| | | Local | | Systemic | | Respiratory |
| Group | NA dose | Mild | Moderate | Mild | Moderate | Mild/Moderate |
| A | 2.6 μg | 3 (15) | 0 | 4 | 0 | 4 |
| B | 7.7 μg | 3 (15) | 0 | 2 | 0 | 1 |
| C | 23.2 μg | 6 (30) | 1 | 4 | 0 | 6 |
| D | 69.9 μg | 11 (55) | 0 | 2 | 0 | 3 |
| E | Tri-Vacc | 11 (55) | 3 | 2 | 0 | 2 |

Table 4 below shows results of NA-supplementation of standard vaccine study with study design and serologic response to immunization. Table 4 also illustrates that a NA-supplemented vaccine has increased NA-immunogenicity as compared to conventional vaccine. Table 4 further shows there is no NA-suppression of the HA-immune response in the NA-supplemented vaccine.

TABLE 4

NA-Supplementation of Standard Vaccine Study In Mouse
Part II: Study Design & Serologic Response to Immunization

| | | | Bleedings | | | | |
| | | | d7 | | d28 | | Challenge |
| Group | Antigen | Boost | NI | HI | NI | HI | D30 |
|---|---|---|---|---|---|---|---|
| 1 | N2 | | 7.1 | <1 | 7.0 | <1 | |
| 2 | H3N2 | | 4.1 | 4.4 | 4.1 | 3.8 | A\JH\33\94 (R) |
| | | | | | | | Or |
| 3 | H3N2 + N2 | | 8.9 | 4.3 | 8.7 | 3.8 | A\Leningrad\360\86 (R) |
| | | | | | | | Or |
| | | | | | | | A\Beijing\32\92 (R) |
| 4 | PBS | | <4 | <1 | <4 | <1 | |

Conclusions:
1) NA-supplemented vaccine has increased NA-immunogenicity compared to conventional vaccine.
2) NA-suppression of the HA-immune response is not observed in the NA-supplemented vaccine.

Table 5 below provides effects on infection in vitro of antibody induced by NA-supplementation of standard vaccine. Data in Table 5 shows that NA-supplemented vaccine can induce both neutralizing and plaque size reducing antibody in equal amount in order to provide a balanced immune response.

TABLE 5

NA-Supplementation of Standard Vaccine Study in Mouse
Part II: Effects of Induced Antibody on Infection in vitro

| Group: | H3N2 Virus Plaque Inhibition | H6N2 Virus Plaque Size Reduction |
|---|---|---|
| 1) N2 | 108 | 22,239 |
| 2) H3N2 | 20,892 | 2,648 |
| 3) H3N2 + N2 | 25,856 | 30,116 |
| 4) PBS | N/O | N/O |

Conclusion:
1) NA-supplemented vaccine induces both neutralizing and plaque size reducing antibody in equal amount to provide a balanced immune response.

Table 6 below provides responses to infection in a NA-supplementation of standard vaccine study by mean pulmonary virus titers. Table 6 shows that NA-supplemented vaccine is protective against a homotypic challenge. Table 6 further shows that a NA-supplemented vaccine according to the present invention induces an immunity that reduces viral replication in heterovariant viral challenge.

TABLE 6

NA-Supplementation of Standard Vaccine Study in Mouse
Part II: Response to Infection-Mean Pulmonary Virus Titers

| | | Challenge Virus: | |
| | Homotypic | Heterotypic | |
| Group: | A\JH\33\94 | A\Beijing\32\92 | A\LN\360\86 |
|---|---|---|---|
| 1)N2 | $1.1 \times 10^2$ (5/5) | $2.1 \times 10^2$ (5/5) | $4.6 \times 10^4$ (5/5) |
| 2)H3N2 | -0- (0/5) | $4.5 \times 10^4$ (5/5) | $5.8 \times 10^5$ (5/5) |
| 3)H3N2 + N2 | -0- (0/5) | $1.0 \times 10^2$ (5/5) | $4.2 \times 10^3$ (5/5) |
| 4)PBS | $4.5 \times 10^5$ (5/5) | $2.0 \times 10^6$ (5/5) | $1.1 \times 10^6$ (5/5) |

Conclusions:
1) NA-supplemented vaccine is protective against a homotypic challenge.
2) Further, the NA-supplemented vaccine induces an immunity that reduces viral replication in heterovariant viral challenge.

Table 7 below provides characteristics of N-(P-Aminophenyl) oxamic acid/agarose.

TABLE 7

N-(p-AMINOPHENYL) OXAMIC ACID/AGAROSE

Matrix: 4% beaded agarose

Activation: cyanogen bromide

Attachment: amino

Spacer: 20 atoms

Binding capacity: approx. 50 units neuraminidase per ml

Form: suspension in 0.1 M NaCl, 0.02% thimerosal

TABLE 7-continued

N-(p-AMINOPHENYL) OXAMIC ACID/AGAROSE

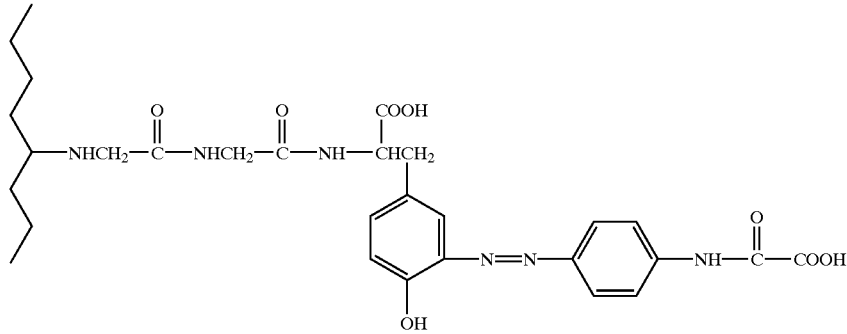

Table 8 below provides formulations for making a purified neuraminidase clinical vaccines, components and amount of components in the vaccines, (e.g., for use in clinical study).

TABLE 8

PURIFIED NEURAMINIDASE CLINICAL VACCINE FORMULATIONS

| 1 Volume | | 1 Volume | | Vaccine Formulations for Clinical Trial Arms |
|---|---|---|---|---|
| 2× Tri-vac | + | CaCl Buffer | = | (1) *Tri-vac |
| 2× Tri-vac | + | 60 μg NA | = | (2) *Tri-vac + 15 μg NA |
| 2× Tri-vac | + | 180 μg NA | = | (3) *Tri-vac + 45 μg NA |
| PBS | + | 60 μg NA | = | (4) 15 μg NA |
| PBS | + | 180 μg NA | = | (5) 45 μg NA |
| PBS | + | CaCl Buffer | = | (6) Placebo (control) |

*Vaccine dose are 0.5 ml and contain 15 μg HA per strain (45 μg HA total)

Table 9 below provides a protocol for testing purified NA.

TABLE 9

TESTING - PURIFIED NA

HA Content
NA Content
NA Enzymatic Activity
Sterility
SDS PAGE
Thimerosal
Oxamic Acid Table 10 below provides a protocol for testing-2×Trivac.

TABLE 10

TESTING - 2 × TRIVAC

HA Content
NA Content
NA Enzymatic Activity
Sterility
LAL

Table 11 below provides a protocol for testing final bulk vaccine with NA, Trivac and Trivac+NA formulations.

TABLE 11

TESTING - FINAL BULK VACCINE (NA, Trivac, and Trivac + NA Formulations)

| | |
|---|---|
| HA Content | Formaldehyde |
| NA Content | Ovalbumin |
| NA Enzymatic Activity | Osmolality |
| Virus Inactivation | Sodium Chloride |
| Sterility | Thimerosal |
| Protein | Triton X-100 |
| Ph | Citrate |
| LAL | |

Table 12 below provides a protocol for testing final bulk vaccine with placebo formulation.

TABLE 12

TESTING - FINAL BULK VACCINE (Placebo Formulation)

Sterility
Ph
LAL
Osmolality
Thimerosal
Protein
General Safety

Table 13 below provides a protocol for testing final container vaccine.

TABLE 13

TESTING - FINAL CONTAINER VACCINE

Sterility
Volume
Homogeneity/Syringeability
Color/Clarity/Particulates
Identity (NA, HA, and Calcium Content)
General Safety Table 14 provides clinical trial design for 300 subjects wherein 60 subjects are vaccinated and observed for 7 days prior to vaccinating the remaining 240 subjects.

TABLE 14

CLINICAL TRIAL DESIGN

| Number of Volunteers | Vaccine Volume | Vaccine | N2 NA (μg) Trivac[1] | N2 NA (μg) Supplement | Total N2 NA (μg) |
|---|---|---|---|---|---|
| 50 | 0.5 ml | Trivac | 7 | — | 7 |
| 50 | 0.5 ml | Trivac + 15 μg NA | 7 | 15 μg | 22 |
| 50 | 0.5 ml | Trivac + 45 μg NA | 7 | 45 μg | 52 |
| 50 | 0.5 ml | N2 (15 μg NA) | | 15 μg | 15 |
| 50 | 0.5 ml | NS (45 μg NA) | | 45 μg | 45 |
| 50 | 0.5 ml | PBS | — | — | — |

[1]Licensed trivalent formulation for '95–'96 containing 15 μg HA each of A/Texas/36/91 (H1N1), A/Johannesburg/33/94 (H3N2), and B/Harbin/7/94. The N2 NA content is estimated to be 7 μg but will be determined experimentally.
Randomized, double blind
60 subjects (10/group) are vaccinated and observed for 7 days prior to vaccinating the remaining 240 subjects Table 15 below provides a protocol for testing immunogenicity.

TABLE 15

IMMUNOGENICITY

Subjects have blood specimens drawn for testing before vaccination and at weeks 1, 2, 3, 4, 10 and 25.
Sera is tested for antibody responses by the following tests for all three virus strains contained in the vaccine.
1. Neuraminidase EIA
2. Neuraminidase inhibition
3. Hemagglutinin ELA
4. Hemagglutination inhibition (HI)
5. Plaque inhibition assays (size and number)

Table 16 below provides a protocol for monitoring adverse event.

TABLE 16

ADVERSE EVENT MONITORING

Observed by study staff on days 0 and 1
Diary kept through day 6 for local and systemic reactions
History for adverse events taken at weekly intervals until week four
CBC and chemistry screen done on days 0 and 7

Table 17 below provides a protocol for Phase III study of the present invention.

TABLE 17

PHASE III STUDY

A challenge study with virulent virus is conducted on a subset (10/group) of a trivalent vaccine plus NA supplement group, the trivalent vaccine group and the placebo group.
The challenge virus can be an H3N2 strain in which the subjects have had no past evidence of infection.
The subjects are observed for clinical evidence of infection, virus shedding and antibody response.

Tables 18 and 19 below show that NA-supplemented vaccine according to the invention is highly NA immunogenic, that this enhanced NA response did not reduce the anti-HA immune response, and that conventional H3N2 vaccine groups had only a modest 1 to 2 $\log_{10}$ reduction in pulmonary virus titers.

TABLE 18

NA-Supplementation of Standard Vaccine Study
Part I: Summary Sheet

| | Pre-Boost[e] | | Post-Boost | | | | | | | | | |
|---|---|---|---|---|---|---|---|---|---|---|---|---|
| | 1° | | | d7 | | d14 | | d21 | | d28 | |
| Group: | NI | HI | Boost[f] | NI | HI | NI | HI | NI | HI | NI | HI |
| 1) —N2[a] | <4 | <1 | | 4.2 | <1 | 6.6 | <1 | 6.5 | <1 | 6.5 | <1 |
| 2) H3N2[b] | <4 | <1.5 | | <4 | 4.1 | 4.2 | 4.0 | 4.1 | 4.0 | 4.0 | 3.2 |
| 3) H3N2[c] | <4 | 2.0 | | <4 | 4.5 | <4 | 4.1 | <4 | 4.0 | <4 | 3.8 |
| 4) H3N2 + N2[d] | 4.1 | 1.2 | | 6.2 | 4.0 | 8.7 | 3.8 | 8.0 | 4.0 | 8.0 | 3.8 |

[a]10 immunologically naive mice received intraperitoneal (i p) injection with 10 μg purified N2-NA from X-118
[b]Commercially produced monovalent H3N2 (X-117) A/Beijing/32/92) split vaccine adjusted to 10 μm NA per dose
[c]Commercially produced monovalent H3N2 (X-117) split vaccine adjusted to equivalent total protein of 10 μg, therefore contained 4 μg NA per dose
[d]Vaccine used in H3N2 (Group 2) with the addition of 10 μg of NA
[e]Numbers are geometric mean endpoint titers of duplicate assays
[f]Mice boosted on 14 day by i p injection of 1 μg of N2, H3N2 split vaccine diluted to contain 1 μg of N2, or 1.1 mixture of H3N2 and N2 (therefore contained 2 μg of N2-NA)
[g]Antigenic relatedness (HA/NA)

| | Sh94 | Be 92 | Le 86 |
|---|---|---|---|
| Johannesberg 94 | | 17/55 | 8/13 |
| Beijing 92 | | | <1/50 |

TABLE 19

Heterovariant Viral Challenge[g]:

| Group | I/T[h] | PFU[i] |
|---|---|---|
| 1) N2[a] | 5/5 | $2.4 \times 10^2$ |
| 2) H3N2[b] | 5/5 | $3.6 \times 10^4$ |
| 3) H3N2[c] | 5/5 | $1.2 \times 10^5$ |
| 4) H3N2 + N2[d] | 5/5 | $3.8 \times 10^2$ |
| 5) PBS[j] | 5/5 | $1.6 \times 10^6$ |

[g]Intranasal inoculation of 100 $MID_{30}$ Mouse Adapted A/Leningrad/360/86 (R), HA 0.8% and NA 50% antigenically related to X-117 by Archelti-Horsfall method.
[h]Number infected/total mice in group
[i]plaque forming united, numbers are mean endpoints of duplicate serial dilutions of lung preparations in MDCK cells.
[j]phosphate buffered saline, the mock infected group.

Tables 20 and 21, below, show that NA-supplemented vaccine according to the invention has increased NA-immunogenicity as compared to conventional vaccine and no suppression of the HA immune response was observed.

TABLE 20

NA-Supplementation of Standard Vaccine Study
Part II: Serologic Response to Immunization

| | | | Bleedings | | | | Challenge |
|---|---|---|---|---|---|---|---|
| | | | d7 | | d28 | | |
| Group: | Antigen | Boost[f] | NI | HI | NI | HI | d30 |
| 1 | N2 10 μg | | 7.1 | <1 | 7.0 | <1 | |
| 2 | H3 10 μg | | <4 | 5.3 | <4 | 4.3 | Mouse Adapted[F]: |
| 3 | H3N2[a] | | 4.1 | 4.4 | 4.1 | 3.8 | A/JH/33/94 (R) |
| | | | | | | | or |
| 4 | H3N2[b] | | 5.4 | 4.9 | 5.1 | 4.0 | A/Beijing/32/92 (R) |
| | | | | | | | Or |
| 5 | H3N2 + N2[c] | | 8.9 | 4.3 | 8.7 | 3.8 | A/Leningrad/360/86 (R) |
| 6 | PBS[d] | | <4 | <1 | <4 | <1 | |

[a]Commercial Vaccine <4 μg NA + HA 10 μg
[b]Commercial Vaccine NA 10 μg i e normalized to Group INA
[c]Commercial Vaccine as in #3 + NA 10 μg
[d]phosphate buffered saline
[e]Numbers are geometric mean titers of duplicate assays with 15 mice per group
[f]Mice boosted on 14 day by i p injection of 1 μg of N2, H3N2 split vaccine diluted to contain 1 μg of N2, or 1.1 mixture of H3N2 and N2 (therefore contained 2 μg of N2-NA)
[g]Anitgenic relatedness (HA/NA)

| | Sh94 | Be 92 | Le 86 |
|---|---|---|---|
| Johannesberg 94 | | 17/55 | 8/13 |
| Beijing 92 | | | <1/50 |

TABLE 21

NA-Supplementation of Standard Vaccine Study
Part II: Study Design & Serologic Response to Immunization

| | | | Bleedings | | | | Challenge |
|---|---|---|---|---|---|---|---|
| | | | d7 | | d28 | | |
| Group: | Antigen | Boost | NI | HI | NI | HI | d30 |
| 1 | N2 | | 7.1 | <1 | 7.0 | <1 | |
| 2 | H3N2 | | 4.1 | 4.4 | 4.1 | 3.8 | A/JH/33/94 (R) |
| | | | | | | | or |
| 3 | H3N2 + N2 | | 8.9 | 4.3 | 8.7 | 3.8 | A/Leningrad/360/86 (R) |
| | | | | | | | or |
| 4 | PBS | | <4 | <1 | <4 | <1 | A/Beijing/32/92 (R) |

CONCLUSIONS:
1) NA-supplemented vaccine has increased NA-immunogenicity compared to conventional vaccine.
2) NA-suppression of the HA-immune response is not observed in the NA-supplemented vaccine Table 22, below shows vaccine formulations and provides an outline of clinical trial for neuraminidase-supplemental influenza vaccine according to the invention.

TABLE 22

| Neuraminidase-Supplemental Influenza Vaccine Clinical Trial Outline | | | | | |
|---|---|---|---|---|---|
| Number of Volunteers | Vaccine Volume | Vaccine | NA (μg) Trivac | NA (μg) Supplement | Total NA (μg) |
| 50 | 0.5 ml | Trivac | 7 | — | 7 |
| 50 | 0.5 ml | Trivac + 15 μg NA | 7 | 15 μg | 22 |
| 50 | 0.5 ml | Trivac + 45 μg NA | 7 | 45 μg | 52 |
| 50 | 0.5 ml | N2 (15 μg NA) | | 15 μg | 15 |
| 50 | 0.5 ml | N2 (45 μg NA) | | 45 μg | 45 |
| 50 | 0.5 ml | PBS | | — | — |

Results parallel those obtained in the mouse model, set forth above.

Tables 23 and 24, below, provide data that demonstrate that the supplemented vaccine according to the invention induces both plaque inhibiting (neutralizing) and plaque size reducing antibody in equal amounts, providing a balanced immune response (compare Group 3 to Group 1 and 2).

TABLE 23

NA-Supplementation of Standard Vaccine Study
Part II: Effects of Induced Antibody on Infection in vitro

| Group: | H3N2 Virus[e] Plaque Inhibition | H6N2 Virus Plaque Size Reduction | H6N2 Virus[g] Plaque Size Reduction |
|---|---|---|---|
| 1) N2 10 μg | 108[f] | 26172 | 22239 |
| 2) H3 10 μg | 32839 | N/O | N/O |
| 3) H3N2[a] | 20892 | N/O | 2648 |
| 4) H3N2[b] | 30866 | N/O | 5479 |
| 5) H3N2 + N2[c] | 25856 | 42960 | 30116 |
| 6) PBS[d] | N/O | N/O | N/O |

[a]Commercial Vaccine 4 μg NA + HA 10 μg
[b]Commercial Vaccine NA 10 μg ie normalized to Group INA
[c]Commercial Vaccine as in #30 NA 10 μg
[d]phosphate buffered saline
[e]Test virus was A/Johannesberg/33/94 (R)
[f]15 mice per group, numbers are arithmetic mean titers of serial dilution of antisera duplicate plates, N/O, None observed
[g]Test virus was A/Turkey/Mass/G/76 x Beijing/32/92 (R)
[h]Antigenic relatedness (HA/NA)

| | Jh94 | Be 92 | Le 86 |
|---|---|---|---|
| Johannesberg 94 | | 17/55 | 8/13 |
| Beijing 92 | | | <1/50 |

TABLE 24

NA-Supplementation of Standard Vaccine Study
Part II: Effects of Induced Antibody on Infection in vitro

| Group | H3N2 Virus Plaque Inhibition | H6N2 Virus Plaque Size Reduction |
|---|---|---|
| 1) N2 | 108 | 22,239 |
| 2) H3N2 | 20,892 | 2,648 |
| 3) H3N2 + N2 | 25,856 | 30,116 |
| 4) PBS | N/O | N/O |

CONCLUSION:
1) NA-supplemented vaccine induces both neutralizing and plaque size reducing antibody in equal amount to provide a balanced immune response.

Tables 25 and 26 below show that NA-supplemented vaccine according to the invention is protective against a homotypic challenge; and, they further show that the NA-supplemented vaccine according to the invention induces an immunity that reduces viral replication>100 fold in heterovariant viral challenge.

TABLE 25

NA-Supplementation of Standard Vaccine Study
Part II: Response to Infection-Mean Pulmonary Virus Titers

| | Challenge Virus[f]: | | |
|---|---|---|---|
| | Homotypic | Heterotypic[g] | |
| Group: | A/JH/33/94 | A\Beijing\32\92 | A\LN\360\86 |
| 1) N2 10 μG | $1.1 \times 10^2$ (5/5)[e] | $2.1 \times 10^2$ (5/5) | $4.6 \times 10^4$ (5/5) |
| 2) H3 10 μg | -0- (0/5) | $3.2 \times 10^4$ (4/5) | $6.2 \times 10^5$ (5/5) |
| 3) H3N2[a] | -0- (0/5) | $4.5 \times 10^4$ (5/5) | $5.8 \times 10^5$ (5/5) |
| 4) H3N2[b] | -0- (0/5) | $2.2 \times 10^4$ (5/5) | $3.2 \times 10^4$ (5/5) |
| 5) H3N2 + N2[c] | -0- (0/5) | $1.0 \times 10^2$ (5/5) | $4.2 \times 10^3$ (5/5) |
| 6) PBS[d] | $4.5 \times 10^5$ (5/5) | $2.0 \times 10^6$ (5/5) | $1.1 \times 10^6$ (5/5) |

[a]Commercial Vaccine <4 μg NA + HA 10 μg
[b]Commercial Vaccine NA 10 μg ie normalized to Group 1NA
[c]Commercial Vaccine as in #3 + NA 10 μg
[d]phosphate buffered saline
[e]5 mice per group, numbers are arithmetic mean titers of duplicate serial dilutions of lung preparations in MDCK cells, (#infected/total)
[f]Intranasal instillation under light anesthesia of 100 $MID_{50}$ of mouse adapted virus
[g]Antigenic relatedness (HA/NA)

| | Jh94 | Be 92 | Le 86 |
|---|---|---|---|
| Johannesberg 94 | | 17/55 | 8/13 |
| Beijing 92 | | | <1/50 |

TABLE 26

NA-Supplementation of Standard Vaccine Study
Part II: Response to Infection-Mean Pulmonary Virus Titers

| | Challenge Virus: | | |
|---|---|---|---|
| | Homotypic | Heterotypic | |
| Group: | A\JH/33/94 | A\Beijing\32\92 | A\LN\360\86 |
| 1) N2 | $1.1 \times 10^2$ (5/5) | $2.1 \times 10^2$ (5/5) | $4.6 \times 10^4$ (5/5) |
| 2) H3N2 | -0- (0/5) | $4.5 \times 10^4$ (5/5) | $5.8 \times 10^5$ (5/5) |
| 3) H3N2 + N2 | -0- (0/5) | $1.0 \times 10^2$ (5/5) | $4.2 \times 10^3$ (5/5) |
| 4) PBS | $4.5 \times 10^5$ (5/5) | $2.0 \times 10^6$ (5/5) | $1.1 \times 10^6$ (5/5) |

Conclusions:
1) NA-supplemented vaccine is protective against a homotypic challenge.
2) Further, the NA-supplemented vaccine induces an immunity that reduces viral replication in heterovariant viral challenge.

Example 4

Johansson et al. in *Journal of Virology*, vol. 67 (10) pp. 5721–5723 (1993), herein incorporated by reference, compared the effects of the vaccine composition set forth in Table 1, wherein the NA:HA ratio varied from 0.1 (no neuraminidase, purified HA only) to 1:1 to 10:1 (added neuraminidase), as well as setting forth methods of immunizing a subject with said compositions. The data reported therein are reproduced below:

TABLE 27

Effects of HA-NA combinations an HI and NI antibody response and challenge infection[a]

| Group | Dose 1 NA ($\mu$g) | Dose 1 HA ($\mu$g) | Dose 2 NA ($\mu$g) | Dose 2 HA ($\mu$g) | Antibody vs: HA ($\log_2$ HI titer) | Antibody vs: NA ($\log_2$ NI titer) | PVT ($\log_{20}$ EID$_{50}$) | No. infected/total |
|---|---|---|---|---|---|---|---|---|
| A1 | | 10.0 | 1.0 | | 3.0 | <2.0 | 1.4 | 2/5 |
| A2 | | 10.0 | 1.0 | 1.0 | 5.2 | <2.0 | <1.0 | 0/5 |
| B1 | 10.0 | 10.0 | 1.0 | | 3.2 | 7.0 | 1.2 | 1/5 |
| B2 | 10.0 | 10.0 | 1.0 | 1.0 | 5.0 | 7.1 | <1.0 | 0/5 |
| C1 | 10.0 | 5.0 | 1.0 | | 2.0 | 7.7 | 4.5 | 3/3 |
| C2 | 10.0 | 5.0 | 1.0 | 1.0 | 4.6 | 7.1 | <1.0 | 0/5 |
| D1 | 10.0 | 2.5 | 1.0 | | <1.0 | 8.0 | 4.3 | 5/5 |
| D2 | 10.0 | 2.5 | 1.0 | 1.0 | 2.0 | 7.5 | 3.8 | 5/5 |
| E1 | 10.0 | 1.0 | 1.0 | | <1.0 | 6.9 | 4.1 | 5/5 |
| E2 | 10.0 | 1.0 | 1.0 | 1.0 | 1.2 | 6.8 | 4.3 | 5/5 |
| F1 | 10.0 | | 1.0 | | <1.0 | 7.6 | 4.0 | 5/5 |
| F2 | 10.0 | | 1.0 | 1.0 | <1.0 | 7.4 | 4.0 | 5/5 |
| G | | | | | <1.0 | <2.0 | 7.5 | 10/10 |

[a]Mice were primed (day 0) and boosted (day 42) with different combinations of purified HA and NA and then tested on day 56 for serologic antibody response to both antigens. Three days after subsequent infection, on day 59, the presence of pulmonary virus and PVT (50% egg infective dose [EID$_{50}$] were determined.

As demonstrated therein, the compositions were sufficient to provoke an immune response.

Having thus described embodiments of the present invention, it is to be understood that the invention defined by the appended claims is not limited by the detailed preferred embodiments as many variations thereon are possible, without departing from the spirit or scope of the invention.

REFERENCES 1. 1993 U.S. and 1993 European Pharmacopoeia, CFR, Licensing Commitments.
2. Ada, G., G. Alexandrova, R. B. Couch, W. R. Dowdle, A. P. Kendal, K. Nerome, G. C. Schild, J. J. Skehel, O. Tomori, and D. A. J. Tyrrell, (1987). Progress in the development of influenza vaccines: Memorandum from a WHO meeting. Bull. WHO. 65: 289–93.
3. Air, G. M., M. C. Ellis, L. E. Brown, W. G. Laver, and R. G. Webster, (1985); Location of antigenic sites on the three-dimensional structure of the influenza N2 virus neuraminidase. Virology. 145:237–48.
4. Bachmeyer, Intervirology, 5,260–272, (1975); an anionic detergent such as ammonium deoxycholate.
5. Barker, W. H. and J. P. Mullooly, (1980); Influenza vaccination of elderly persons: Reduction in pneumonia and influenza hospitalization and deaths. JAMA 244: 2547–9.
6. Bentley, D. R. en Brownlee, G. G., (1982); Sequence of the N2 neuraminidase from influenza virus A/NT/60/68, Uncle. Acids. Res. 10, 5033.
7. Brown, J. and Laver, W. G., (1968); The effect of antineuraminidase antibody on the elution of influenza virus from cells, *J. Gen. Virol.*: 2, 291.
8. Bucher and Kilbourne, (1972); Laver and Valentine, (1969); Varghese et al., (1983); Ward et al., (1983).
9. Burnet, F. M., Stone, J. D., (1947) The receptor destroying enzyme of V. cholerae, Aust. J. Exp. Biol. Med. Sci. 25, 227–233.
10. Cerini, C., A. Joseph, G. Kalish, M. Kahn, W. Kutzner, M. Stebbins, D. McCoy, (1981). Efficacy of neuraminidase specific H7N1 influenza vaccine in an influenza H1N1 outbreak. Curr. Chemotherapy & Immunotherapy, Proc. 12th International Congress of Chemotherapy, Florence, Italy, July, 1981.
11. Chong, A., et al., Biochemica et Biophysica Acta 1077:65–71.
12. Clements, M. L., R. L. Betts, R. L. Tierney, and B. R. Murphy, (1986). Serum and nasal wash antibodies associated with resistance to experimental challenge with influenza A wild-type virus. J. Clin. Microbiol. 22:157–60.
13. Clements, "Influenza Vaccines", in *Vaccines: New Approaches to Immunological Problems*, ed. Ronald W. Ellis, pp. 120–150 (Butterworth-Heinemann, Stoneham, Mass. 1992).

14. Colman, P. M., Varghese, J. N. & Laver, W. G., (1983); Structure of the catalytic and antigenic sites in influenza virus neuraminidase, Nature 303, 41–44.
15. Colman, P. M. & Ward, C. W., (1985); Structure and diversity of influenza neuraminidase, Curr. Top. Microbiol. Immunol. 114, 177255.
16. Couch, R. B., J. A. Kasel, .L. Gerin, J. L. Schulman, and E. D. Kilbourne, (1974); Induction of partial immunity to influenza by a neuraminidase-specific influenza A virus vaccine in humans. J. Infect. Dis. 129: 411–20.
17. Couch, R. B. and J. A. Kasel. Immunity to influenza in man, (1983); Annu. Rev. Microbiol. 37:529–49.
18. Davies, J. R. and E. A. Grilli, (1989); Natural or vaccine induced antibody as a predictor of immunity in the face of natural challenge with influenza viruses. Epidemiol. Inf. 102:325–33.
19. Devenport, F. M., Hennessy, A. V., Brandon, F. M., Webster, R. G., Barrett, C. D. & Lease, G. O., (1964); Comparisons of serological and febrile responses in humans to vaccination with influenza A viruses or their hemagglutinins, J. Lab. Clin. Med.: 63,5.
20. Dowdle, W. R., (1981); Influenza immunoprophylaxis after 30 years experience. In Genetic Variation Among Influenza Viruses—ICN-UCLA Symposia on Molecular and Cellular Biology, ed. D. P. Nagle, C. F. Fox, Vol. XXI: 525–34. New York; Academic Press.
21. Dowdle, W. R., M. T. Coleman, S. R. Mostow, H. S. Kaye, S. C. Schoenbaum, (1973); Inactivated influenza vaccines: 2 laboratory indices of protection. Postgrad. Med. J. 49:159–63.
22. PNAS 84:6869–6873.
23. Blok, J., Air, G. M., Laver, W. G., Ward, C. W., Lilley, G. G., Woods, E. F., Roxburgh, C. M. & Inglis, A. S. (1982) Studies on the size, chemical composition and partial sequence of the neuraminidase (NA) from type A influenza virus show that the N-terminal region of the NA is not processed and serves to anchor the NA in the viral membrane, Virology, 119, 109–121.
24. Francis, T. Jr., F. M. Davenport and A. V. Hennessy, (1953); A serological recapitulation of human infection with different strains of influenza virus. Trans. Assoc. Am. Phys. 66:231–8.
25. French patent 2 201 079.
26. Gallagher, M., Bucher, D. J., Dourmashkin, R., Davis, J. F., Rosenn, G. & Kilbourne, E. D., (1984); Isolation of immunogenic neuraminidoses of human influenza viruses by a combination of genetic and biochemical procedures, J. Clin. Microbiol., 20, 89 to 93.
27. Gill, P. W., N. F. Babbage, P. E. Gunton, W. Flower, and D. A. Garrett, (1971); Did the Asian virus protect us from Hong Kong influenza? Med. J. Aust. 2:53–4.
28. Gottschalk, A., (1957); The specific enzyme of influenza virus and vibrio cholerae, Biochim. Biophys. Acta 23, 645–646.
29. Grand and Skehel, (1972); Nature, New Biology, Vol. 238, 145–147.
30. Hirst, G. K., (1942); The quantitative determination of influenza virus and antibodies by means of red cell aqqlutination, J. Exp. Med.: 75, 47.
31. Jahiel, R. I. and Kilbourne, E. D., (1966); Reduction in plague size and reduction in plague number as differing indices of influenza virus-antibody reaction, J. Bacteriol. :92, 1521–1534.
32. Johansson, B. E., T. M. Moran, C. A. bona, and E. D. Kilbourne, (1987b); Immunologic response to influenza virus neuraminidase is influenced by prior experience with associated viral hemagglutinin. III. Reduced generation of neuraminidase-specific helper T cells in hemagglutinin-primed mice. J. Immunol. 139: 2015–19.
33. Johansson et al., J. Virology, 63:1239–1246 (1989).
34. Johansson, B. E. and E. D. Kilbourne, (1994); Immunization with purified N1 and N2 influenza virus neuraminidases demonstrates cross-reactivity without antigenic competition. Proc. Natl. Acad. Sci. USA. 91:2358–61.
35. Johansson, B. E., D. J. Bucher, E. D. Kilbourne, (1989); Purified influenza hemagglutinin and neuraminidase are equivalent in stimulation of antibody response but induce contrasting types of immunity to infection. J. Virol. 63: 1239–46.
36. Johansson, B. E. and E. D. Kilbourne, (1990); Comparative long-term effects in a mouse model system of influenza whole virus and purified neuraminidase vaccines followed by sequential infections. J. Infect. Dis. 162: 800–09.
37. Johansson, B. E., T. M. Moran, E. E. Kilbourne, (1987c); Antigen-presenting B cells and Th cells cooperatively mediate intravironic antigenic competition between influenza A virus surface glycoproteins. Proc. Natl. Acad. See. USA. 84:6869–73.
38. Johansson, B. E. T. M. Moran, C. A. Bona, S. W. Popple, and E. D. Kilbourne, (1987a); Immunologic response to influenza virus neuraminidase is influenced by prior experience with the associated hemagglutinin. II. Sequential infection of mice simulates human experience. J. Immunol. 139:2010–14.
39. Johansson, B. E. and E. D. Kilbourne, (1993); Dissociation of influenza virus hemagglutinin and neuraminidase eliminates their intravironic antigenic competition. J. Virol. 67: 5721–3.
40. Kendal, A. P., F. M. Bozeman, and F. A. Ennis, (1980); Further studies of the neuraminidase content of inactivated influenza vaccines and the neuraminidase antibody responses after vaccination of immunologically primed an un-primed populations. Infect. Immun. 29:966–71.
41. Kendal, A., et al., Inf. Immun., 20:966–971.
42. Kida, H., Webster, R. B. & Yanagawa, R., (1983); Inhibition of virus-induced hemolysis with monoclonal antibodies to different antigenic areas on the hemagglutinin molecule of A/Seal/Massachusetts/1/80 (H7N7) influenza virus, Arch. Virol., 76, 91 to 99.
43. Kilbourne, E. D., B. E. Johansson, and B. Grajower, (1990); Independent and disparate evolution in nature of influenza A virus hemagglutinin and neuraminidase. Proc. Natl. Acad. Sci. USA. 87:786–90.
44. Kilbourne, E. D., W. G. Laver, J. C. Schulman, and R. G. Webster, (1975); Antiviral activity of antiserum specific for an influenza virus neuraminidase. J. Virology 2:281–9.
45. Kilbourne, E. D., R. B. Couch, J. A. Kasel, W. A. Keitel, T. R. Cate, J. H. Quarles, B. Grajower, B. A. Pokorny and B. E. Johansson (1995); Purified influenza A virus N2 neuraminidase vaccine is immunogenic and non-toxic in humans. Vaccine, 18, 1799–1803.
46. Kilbourne, E. D., (1976); Comparative efficacy of neuraminidase-specific and conventional influenza virus vaccines in the induction of anti-neuraminidase antibody in man. J. Infect. Dis. 134: 384–94.
47. Kilbourne, E. D., Laver, W. G., Schulman, J. L. & Webster, R. G., (1968); Antiviral activity of antiserum specific for an influenza virus neuraminidase, J. Virol., 2, 281-288.
48. Kilbourne, E. D., C. P. Cerini, M. W. Khan, J. W. Mitchell, Jr. and P. L. Ogra., (1987); Immunologic response to the influenza virus neuraminidase is influenced by prior experience with the associated viral hemagglutinin. I. Studies in human vaccines. J. Immunol. 138:3010–13.
49. Kilbourne, E. D., (1976); Comparative efficacy of neuraminidase-specific and conventional influenza virus vaccines in the induction of anti-neuraminidase antibody in man, *J. Infect. Dis.*, 134:384–94.
50. Kim, W., J. Arrobio, C. Brandt, R. Parrot, B. Murphy, D. Richman, and R. Chanock, (1976); Temperature-sensitive mutants of influenza A virus: response of children to the Influenza A/Hong Kong/68-ts-le(H3N2) candidate vaccine viruses and significance of immunity to neuraminidase antigen. Pediatric Research 10:238–42.
51. Kuby, Janis, (1994); Immunology, Second Edition, p. 105.
52. Lamb, R. A. and P. W. Choppin, (1983); The gene structure and replication of influenza virus. Annu. Rev. Biochem. 52: 467–506.
53. Laver & Webster, Virology 69, 511–522, 1976.
54. Liu, C., M. C. Eichelberger, R. W. Campans, and G. M. Air, (1995); Influenza type A virus neuraminidase does not play a role in viral entry, replication, assembly or budding. J. Virology 69:1099–1106.
55. Murphy, R. R. J. A. Kasel, and R. M. Chanock, (1972); Association of serum anti-neuraminidase antibody with resistance to influenza in man. New England J. Med. 286:1329–32.
56. Murphy & Webster, in "Virology, 2nd edition (Fields et al. Ed.) 1091–1152 (1990), in particular p. 1128.
57. Ogra, P. L., T. Chow, K. R. Beutner, E. Rubi, J. Strussenberg, S. DeMello, and C. Rizzone, (1977); Clinical and immunologic evaluation of neuraminidase-specific influenza A virus vaccine in humans. J. Infect. Dis., 135: 499–506.
58. Oxford, J. S., L. R. Haaheim, A. Slepushkin, J. Werner, E. Kuvert, and G. C. Schild, (1981); Strain specificity of serum antibody to the hemagglutinin of influenza A (H3N2) viruses in children following immunization or natural infection. J. Hyg. Camb. 86:17–26.
59. Oxford, J. S., G. C. Schild, C. W. Potter, and R. Jennings, (1979); The specificity of the antihemagglutinin antibody response induced in man by inactivated influenza vaccines and by natural infection. J. Hyg. Camb. 82:51–61.
60. Palese, P. and J. F. Young, (1982); Variation of influenza A, B and C viruses. Science 215: 1468–74.
61. Palese, P., K. Tobita, M. Ueda, and R. W. Compans, (1974); Characterization of temperature-sensitive influenza virus mutants defective in neuraminidase. Virology 61:397–410.
62. Patriarca, P. A., J. A. Weber, R. A. Parlan, W. N. Hall, A. P. Kendal, D. J. Bregman, and L. B. Schonberger, (1985); Efficacy of influenza vaccine in nursing homes: Reduction in illness and complication during an influenza A (H3N2) epidemic. JAMA 253: 1136–9.
63. Potter, C. W. 1982. Inactivated influenza virus vaccine. in *Basic and Applied Influenza Research* ed. A. S. Beare, pp. 119–56, Miami: CRC Press.
64. Potter, C. W., R. Jennings, J. P. Phair, A. Clark and C. H. Stuart-Harris, (1977); Dose-response relationship after immunization of volunteers with a new, surface-antigen-adsorbed influenza virus vaccine. J. Infect. Dis. 135:423–31.
65. Powers and Belshe, (1993); *J. Inf. Dis.*, 167:584–592.
66. Quinnan, G. V., R. Schooley, R. Dolin, F. A. Ennis, P. Gross, and J. W. Gwaltney, (1983); Serologic responses and systemic reactions in adults after vaccination with monovalent A/USSR/77 and trivalent A/USSR/77, A/Tesas/77, B/Hong Kong/72 influenza vaccines. Rev. Infect. Dis. 5:748–56.
67. Rott, R., Becht, H. & Orlich, M., (1974); The significance of influenza virus neuraminidase in immunity, *J. Gen. Virol.*, 22, 35 to 41.
68. Schulman, J. L., Khakpour, M. & Kilbourne, E. D., (1968); Protective effects of specific immunity to viral neuraminidase on influenza virus infection of mice, *J. Virol.*, 2, 778 to 786.
69. Seto, J. T., Drzeniek, R. & Rott R., (1966); Isolation of a low molecular weight sialidase (neuraminidase) from influenza virus, *Biochem. Biophys. Acta:* 113, 402–404.
70. Skehel J. J., P. M. Bayley, E. B. Brown, S. R. Martin, M. D. Waterfield, J. M. White, I. A. Wilson, D. C. Wiley, (1982); Changes in the conformation of influenza virus hemagglutinin at the Ph optimum of virus-mediated membrane fusion. Proc. Natl. Acad. Sci. USA. 79: 968–72.
71. Sugrue, R. J. and A. J. Hay, (1991); Structural characteristics of the M2 protein of influenza A viruses: evidence that it forms a tetrameric channel. Virology 180:617:24.
72. J. Infect. Dis. 136:412–423 (1976) (Swine Flu).
73. The Journal of Immunology, Vol. 119, 2073–2077, (1977).
74. Varghese, J. N., W. G. Laver, and P. M. Colman, (1983); Structure of the influenza virus glycoprotein antigen neuraminidase at 2.9 A resolution. Nature 303:35–40.
75. Variable NA Content of Licensed Vaccines: H3N2 (Infect. and Immunity 29:966–971)
76. Virelizier, J. L., (1975); Host defenses against influenza: the role of anti-hemagglutinin antibody. J. Immunol. 115:434–9.
77. Vonka, V., H. Zavadova, J. Bruj, V. Skocil, V. Janout, M. Uvizl, and J. Kotikova, (1977); Small-scale field trial with neuraminidase vaccine. Dev. Biolog. Stand. 39: 337–9.
78. Ward, C. W., Elleman, T. C. & Azad, A. A., (1982); Amino Acid sequence of the pronase-released heads of neuraminidase subtype N2 from the Asian Strain A/Tokyo/3/67 of influenza virus, *Biochem, J.:* 207, 91 to 95.
79. Webster, R. G. W. J. Bean, O. T. Gorman, T. M. Chambers, and Y Kawaoka, (1992); Evolution and ecology of influenza A viruses. Microbiol. Rev. 56:152–79.
80. Weis, W., J. H. Brown, S. Cusack, J. C. Paulson, J. J. Skehel, and D. C. Wiley, (1988); Structure of the influenza virus hemagglutinin complexed with its receptor, sialic acid. Nature 333: 426–31.
81. Weis et al., (1988); Structure of the influenza virus hemagglutinin complexed with its receptor, sialic acid" *Nature*, 333:426–431.
82. WHO Bull. 58, 585–591 (1980), and in Murphy & Webster, op. cit.
83. Wiley D. C., I. A. Wilson, and J. J. Skehel, (1981); Structural identification of the antibody-binding sites of Hong Kong influenza hemagglutinin and their involvement in antigenic variation. Nature 289: 373–8.
84. Wilson, et al., (1981); Structure of the hemagglutinin membrane glycoprotein of influenza virus at 3A resolution *Nature* 289:366–378.
85. Wrigley, N. G., Skehel, J. J., Charlwood, P. A. & Brand, C. M., (1973); The size and shape of influenza virus neuraminidase, *Virology* 51, 525–529.

What is claimed is:
1. A method for formulating a vaccine composition which comprises an anti-influenza vaccine, wherein the improvement of the vaccine composition comprises having as an additive:

substantially pure, influenza neuraminidase protein and
wherein influenza hemagglutinin protein is also present in the composition, comprising mixing the anti-influenza vaccine which comprises the influenza hemaglutinin, and the neuraminidase, wherein the neuraminidase protein is present in the composition at a molar ratio of from about 0.05 to 0.3 relative to the hemagglutinin protein present.

2. The method of claim 1, wherein the neuraminidase protein is present in the composition at a molar ratio of from about 0.15 to 0.3 relative to the hemagglutinin protein present.

3. The method of claim 1, wherein the total neuraminidase protein is present in the composition at a molar ratio of from about 0.15 to 0.3 relative to the total hemagglutinin protein present.

4. The method of claim 1, wherein the neuraminidase protein is present in the composition at a molar ratio of from about 0.05 to about 0.15 relative to the hemagglutinin protein present.

5. The method of claim 1, wherein the total neuraminidase protein is present in the composition at a molar ratio of from about 0.05 to about 0.15 relative to the total hemagglutinin protein present.

6. A method for formulating a vaccine composition which comprises an anti-influenza vaccine, wherein the improvement of the vaccine composition comprises having as an additive:

substantially pure, mature, glycosylated influenza hemagglutinin protein and said protein is immunogenic; and,
substantially pure, influenza neuraminidase, comprising mixing the anti-influenza vaccine, the hemagglutinin, and the neuraminidase, wherein the neuraminidase protein is present in the composition at a molar ratio of from about 0.05 to 0.3 relative to the hemagglutinin protein present.

7. The method of claim 6, wherein the neuraminidase protein is present in the composition at a molar ratio of from about 0.15 to 0.3 relative to the hemagglutinin protein present.

8. The method of claim 6, wherein the total neuraminidase protein is present in the composition at a molar ratio of from about 0.15 to 0.3 elative to the total hemagglutinin protein present.

9. The method of claim 6, wherein the neuraminidase protein is present in the composition at a molar ratio of from about 0.05 to about 0.15 relative to the hemagglutinin protein present.

10. The method of claim 6, wherein the total neuraminidase protein is present in the composition at a molar ratio of from about 0.05 to about 0.15 relative to the total hemagglutinin protein present.

* * * * *

UNITED STATES PATENT AND TRADEMARK OFFICE
CERTIFICATE OF CORRECTION

PATENT NO. : 6,951,649 B2
DATED : October 4, 2005
INVENTOR(S) : Gail Eugene Smith et al.

It is certified that error appears in the above-identified patent and that said Letters Patent is hereby corrected as shown below:

Title page,
Item [73], Assignee, "Meridien" should be -- Meriden --.

Column 44,
Line 17, "elative" should be -- relative --.

Signed and Sealed this

Thirty-first Day of January, 2006

JON W. DUDAS
*Director of the United States Patent and Trademark Office*